(12) United States Patent
Schneider et al.

(10) Patent No.: US 11,141,573 B2
(45) Date of Patent: Oct. 12, 2021

(54) METHOD FOR PLAQUE SERRATION

(71) Applicant: CAGENT VASCULAR, INC., Wayne, PA (US)

(72) Inventors: Peter Schneider, Honolulu, HI (US); Robert Giasolli, Orange, CA (US)

(73) Assignee: Cagent Vascular, Inc., Wayne, PA (US)

( * ) Notice: Subject to any disclaimer, the term of this patent is extended or adjusted under 35 U.S.C. 154(b) by 99 days.

(21) Appl. No.: 15/276,575

(22) Filed: Sep. 26, 2016

(65) Prior Publication Data
US 2017/0106174 A1 Apr. 20, 2017

Related U.S. Application Data

(60) Division of application No. 12/562,511, filed on Sep. 18, 2009, now Pat. No. 9,480,826, which is a
(Continued)

(51) Int. Cl.
*A61M 25/10* (2013.01)
*A61B 17/20* (2006.01)
(Continued)

(52) U.S. Cl.
CPC ......... *A61M 25/104* (2013.01); *A61B 17/205* (2013.01); *A61B 17/320725* (2013.01);
(Continued)

(58) Field of Classification Search
CPC .. A61B 17/320725; A61B 2017/22061; A61B 17/22; A61M 2025/109;
(Continued)

(56) References Cited

U.S. PATENT DOCUMENTS 3,221,746 A 12/1965 Noble
3,635,223 A 1/1972 Klieman
(Continued)

FOREIGN PATENT DOCUMENTS

AU 2009226025 9/2009
AU 2015343272 7/2020
(Continued)

OTHER PUBLICATIONS

U.S. Appl. No. 15/316,067, filed Dec. 2, 2016, Giasolli et al.
(Continued)

*Primary Examiner* — Lauren P Farrar
*Assistant Examiner* — Hamza A Darb
(74) *Attorney, Agent, or Firm* — Knobbe, Martens, Olson & Bear, LLP

(57) ABSTRACT

A device and method for intravascular treatment of atherosclerotic plaque prior to balloon angioplasty which microperforates the plaque with small sharp spikes acting as serrations for forming cleavage lines or planes in the plaque. The spikes may also be used to transport medication into the plaque. The plaque preparation treatment enables subsequent angioplasty to be performed at low balloon pressures of about 4 atmospheres or less, reduces dissections, and avoids injury to the arterial wall. The subsequent angioplasty may be performed with a drug-eluting balloon (DEB) or drug-coated balloon (DCB). The pre-angioplasty perforation procedure enables more drug to be absorbed during DEB or DCB angioplasty, and makes the need for a stent less likely. Alternatively, any local incidence of plaque dissection after balloon angioplasty may be treated by applying a thin, ring-shaped tack at the dissection site only, rather than applying a stent over the overall plaque site.

15 Claims, 18 Drawing Sheets

Related U.S. Application Data continuation-in-part of application No. 12/408,035, filed on Mar. 20, 2009, now Pat. No. 8,323,243.

(60) Provisional application No. 61/038,477, filed on Mar. 21, 2008.

(51) Int. Cl.
*A61B 17/3207* (2006.01)
*A61B 17/00* (2006.01)
*A61M 25/00* (2006.01)
*A61B 17/22* (2006.01)
*A61M 37/00* (2006.01)

(52) U.S. Cl.
CPC .... *A61M 25/1011* (2013.01); *A61M 25/1027* (2013.01); *A61B 2017/00004* (2013.01); *A61B 2017/22061* (2013.01); *A61M 2025/0096* (2013.01); *A61M 2025/105* (2013.01); *A61M 2025/109* (2013.01); *A61M 2025/1013* (2013.01); *A61M 2025/1031* (2013.01); *A61M 2025/1059* (2013.01); *A61M 2025/1084* (2013.01); *A61M 2025/1086* (2013.01); *A61M 2037/003* (2013.01); *A61M 2037/0023* (2013.01); *A61M 2037/0046* (2013.01)

(58) Field of Classification Search
CPC ...... A61M 25/0082; A61M 2025/0096; A61M 2025/105; A61M 2025/1086; A61M 25/104; A61M 25/1011; A61M 25/10; A61F 2/84
See application file for complete search history.

(56) References Cited

U.S. PATENT DOCUMENTS

| | | | |
|---|---|---|---|
| 4,465,072 A | 8/1984 | Taheri | |
| 4,665,906 A | 5/1987 | Jervis | |
| 4,699,611 A | 10/1987 | Bowden | |
| 4,795,458 A | 1/1989 | Regan | |
| 4,856,516 A | 8/1989 | Hillstead | |
| 5,009,659 A | 4/1991 | Hamlin | |
| 5,042,707 A | 8/1991 | Taheri | |
| 5,078,736 A | 1/1992 | Behl | |
| 5,192,291 A | 3/1993 | Pannek, Jr. | |
| 5,196,024 A | 3/1993 | Barath | |
| 5,209,799 A | 5/1993 | Vigil | |
| 5,320,634 A | 6/1994 | Vigil et al. | |
| 5,336,234 A | 8/1994 | Vigil | |
| 5,397,355 A | 3/1995 | Marin et al. | |
| 5,411,478 A | 5/1995 | Stillabower | |
| 5,417,707 A | 5/1995 | Parkola | |
| 5,423,851 A | 6/1995 | Samuels | |
| 5,484,411 A | 1/1996 | Inderbitzen et al. | |
| 5,501,689 A | 3/1996 | Green | |
| 5,514,154 A | 5/1996 | Lau et al. | |
| 5,569,272 A | 10/1996 | Reed | |
| 5,591,197 A | 1/1997 | Orth et al. | |
| 5,593,434 A | 1/1997 | Williams | |
| 5,616,149 A | 4/1997 | Barath | |
| 5,665,116 A | 9/1997 | Chaisson | |
| 5,681,346 A | 10/1997 | Orth | |
| 5,713,860 A | 2/1998 | Kaplan et al. | |
| 5,713,863 A | 2/1998 | Vigil et al. | |
| 5,718,684 A | 2/1998 | Gupta | |
| 5,720,726 A | 2/1998 | Marcadis et al. | |
| 5,797,935 A | 8/1998 | Barath et al. | |
| 5,797,951 A | 8/1998 | Mueller | |
| 5,800,526 A | 9/1998 | Anderson | |
| 5,824,053 A | 10/1998 | Khosravi et al. | |
| 5,868,779 A | 2/1999 | Ruiz | |
| 5,957,949 A | 9/1999 | Leonhardt et al. | |
| 6,007,543 A | 12/1999 | Ellis | |
| 6,036,725 A | 3/2000 | Avellanet | |
| 6,048,332 A | 4/2000 | Duffy et al. | |
| 6,053,943 A | 4/2000 | Edwin | |
| 6,102,904 A | 8/2000 | Vigil et al. | |
| 6,126,685 A | 10/2000 | Lenker | |
| 6,197,013 B1 * | 3/2001 | Reed | A61F 2/86 604/103.02 |
| 6,221,102 B1 | 4/2001 | Baker | |
| 6,254,642 B1 | 7/2001 | Taylor | |
| 6,280,414 B1 | 8/2001 | Shah et al. | |
| 6,290,728 B1 | 9/2001 | Phelps | |
| 6,371,962 B1 | 4/2002 | Ellis | |
| 6,485,496 B1 | 10/2002 | Suyker et al. | |
| 6,475,237 B2 | 11/2002 | Drasler | |
| 6,562,062 B2 | 5/2003 | Jenusaitis et al. | |
| 6,626,861 B1 | 9/2003 | Hart et al. | |
| 6,632,231 B2 | 10/2003 | Radisch, Jr. | |
| 6,638,246 B1 | 10/2003 | Naimark et al. | |
| 6,692,504 B2 | 2/2004 | Kurz | |
| 6,719,775 B2 | 4/2004 | Slaker | |
| 6,942,680 B2 | 9/2005 | Garyzel et al. | |
| 7,007,698 B2 | 3/2006 | Thornton | |
| 7,087,088 B2 | 8/2006 | Berg | |
| 7,179,284 B2 | 2/2007 | Khosravi | |
| 7,204,847 B1 | 4/2007 | Gambale | |
| 7,211,101 B2 | 5/2007 | Carley | |
| 7,270,673 B2 | 9/2007 | Yee | |
| 7,279,002 B2 | 10/2007 | Shaw et al. | |
| 7,291,158 B2 | 11/2007 | Crow | |
| 7,303,572 B2 | 12/2007 | Meisheimer | |
| 7,413,558 B2 | 8/2008 | Kelley et al. | |
| 7,500,986 B2 | 3/2009 | Lye et al. | |
| 7,611,484 B2 | 11/2009 | Wellman et al. | |
| 7,691,116 B2 | 4/2010 | Goodin | |
| 7,691,119 B2 | 4/2010 | Farnan | |
| 7,931,663 B2 | 4/2011 | Farnan | |
| 8,192,675 B2 | 6/2012 | Burton et al. | |
| 8,323,243 B2 | 12/2012 | Schnieder et al. | |
| 8,454,637 B2 | 6/2013 | Aggerholm et al. | |
| 8,574,248 B2 | 11/2013 | Kassab | |
| 9,066,749 B2 | 6/2015 | Burton et al. | |
| 9,095,688 B2 | 8/2015 | Burton | |
| 9,119,944 B2 | 9/2015 | Chambers et al. | |
| 9,204,893 B2 | 12/2015 | Rizk et al. | |
| 9,242,076 B2 | 1/2016 | Burton et al. | |
| 9,339,291 B2 | 5/2016 | Aggerholm et al. | |
| 9,393,386 B2 | 7/2016 | Schneider et al. | |
| 9,480,826 B2 | 11/2016 | Schneider et al. | |
| 10,166,374 B2 | 1/2019 | Giasolli et al. | |
| 10,172,729 B2 | 1/2019 | Fulkerson et al. | |
| 10,258,487 B2 | 4/2019 | Fulkerson et al. | |
| 10,300,253 B2 | 5/2019 | Pederson | |
| 10,463,842 B2 | 11/2019 | Giasolli et al. | |
| 10,471,238 B2 | 11/2019 | Schneider et al. | |
| 10,689,154 B2 | 6/2020 | Giasolli et al. | |
| 10,729,892 B2 | 8/2020 | Yamazaki | |
| 2001/0016726 A1 | 8/2001 | Dubrul et al. | |
| 2001/0020151 A1 | 9/2001 | Reed et al. | |
| 2002/0010489 A1 | 1/2002 | Grayzel et al. | |
| 2002/0077594 A1 | 6/2002 | Chien et al. | |
| 2003/0065303 A1 * | 4/2003 | Wellman | A61M 25/1011 604/500 |
| 2003/0153870 A1 | 8/2003 | Meyer et al. | |
| 2003/0158595 A1 | 8/2003 | Randall | |
| 2003/0163148 A1 | 8/2003 | Wang et al. | |
| 2003/0229370 A1 | 12/2003 | Miller | |
| 2004/0098014 A1 | 5/2004 | Flugelman et al. | |
| 2004/0106904 A1 | 6/2004 | Gonnelli et al. | |
| 2004/0143287 A1 | 7/2004 | Konstantino et al. | |
| 2004/0158270 A1 | 8/2004 | Wyzgala et al. | |
| 2004/0186551 A1 | 9/2004 | Kao | |
| 2004/0249445 A1 | 12/2004 | Rosenthal et al. | |
| 2005/0021070 A1 | 1/2005 | Feld et al. | |
| 2005/0137618 A1 | 6/2005 | Kunis | |
| 2005/0149082 A1 | 7/2005 | Yee et al. | |
| 2005/0177130 A1 | 8/2005 | Konstantino et al. | |
| 2005/0203388 A1 | 9/2005 | Carr | |
| 2005/0228343 A1 | 10/2005 | Kelley | |
| 2005/0251164 A1 | 11/2005 | Gifford | |

(56) References Cited

U.S. PATENT DOCUMENTS

| | | |
|---|---|---|
| 2005/0267409 A1 | 12/2005 | Shkolnik |
| 2005/0288764 A1 | 12/2005 | Snow |
| 2006/0015134 A1 | 1/2006 | Trinidad |
| 2006/0085023 A1 | 4/2006 | Davies et al. |
| 2006/0122684 A1 | 6/2006 | Lye et al. |
| 2006/0129093 A1* | 6/2006 | Jackson ......... A61B 17/320725 604/96.01 |
| 2006/0149308 A1 | 7/2006 | Melsheimer |
| 2006/0184191 A1 | 8/2006 | O'Brien |
| 2007/0016232 A1 | 1/2007 | Martin et al. |
| 2007/0021774 A1 | 1/2007 | Hogendijk |
| 2007/0060863 A1 | 3/2007 | Goeken et al. |
| 2007/0093744 A1 | 4/2007 | Elmaleh |
| 2007/0191766 A1 | 8/2007 | McMorrow |
| 2007/0191811 A1 | 8/2007 | Berglund |
| 2007/0213761 A1 | 9/2007 | Murphy et al. |
| 2008/0015500 A1 | 1/2008 | Herweck et al. |
| 2008/0275483 A1* | 11/2008 | Makower ............... A61B 17/24 606/192 |
| 2009/0157159 A1 | 6/2009 | Schneider et al. |
| 2009/0214615 A1 | 8/2009 | Zhao |
| 2009/0227949 A1 | 9/2009 | Knapp et al. |
| 2010/0015196 A1 | 1/2010 | Kimble et al. |
| 2010/0087783 A1 | 4/2010 | Weber et al. |
| 2010/0274188 A1 | 10/2010 | Chang et al. |
| 2010/0274271 A1 | 10/2010 | Kelly |
| 2011/0178503 A1 | 7/2011 | Kangas |
| 2011/0213401 A1 | 9/2011 | Grayzel et al. |
| 2012/0041412 A1 | 2/2012 | Roth et al. |
| 2012/0059401 A1 | 3/2012 | Konstantino et al. |
| 2012/0172901 A1 | 7/2012 | Manderfeld et al. |
| 2012/0277843 A1 | 11/2012 | Weber et al. |
| 2013/0018396 A1 | 1/2013 | Gunderson et al. |
| 2013/0066346 A1 | 3/2013 | Pigott |
| 2013/0110142 A1 | 5/2013 | Bence et al. |
| 2013/0165958 A1 | 6/2013 | Schneider et al. |
| 2013/0190725 A1 | 7/2013 | Pacetti et al. |
| 2013/0211381 A1 | 8/2013 | Feld |
| 2013/0218181 A1 | 8/2013 | Feld et al. |
| 2013/0253426 A1 | 9/2013 | Campbell et al. |
| 2013/0261545 A1 | 10/2013 | Osypka |
| 2014/0066898 A1 | 3/2014 | Cully et al. |
| 2014/0066960 A1 | 3/2014 | Feld et al. |
| 2016/0324538 A1 | 11/2016 | Schneider et al. |
| 2016/0346506 A1 | 12/2016 | Jackson et al. |
| 2017/0080192 A1 | 3/2017 | Giasolli et al. |
| 2017/0100570 A1 | 4/2017 | Giasolli et al. |
| 2017/0333686 A1 | 11/2017 | Schneider et al. |
| 2018/0140804 A1 | 5/2018 | Tsukamoto et al. |
| 2018/0200491 A1 | 7/2018 | Giasolli et al. |
| 2018/0304052 A1 | 10/2018 | Schneider et al. |
| 2019/0240464 A1 | 8/2019 | Giasolli et al. |
| 2019/0262595 A1 | 8/2019 | Ryu et al. |
| 2019/0282789 A1 | 9/2019 | Mayda |
| 2020/0140141 A1 | 5/2020 | Giasolli et al. |
| 2020/0147355 A1 | 5/2020 | Schneider et al. |
| 2020/0155815 A1 | 5/2020 | Giasolli et al. |
| 2020/0188641 A1 | 6/2020 | Giasolli et al. |

FOREIGN PATENT DOCUMENTS

| | | |
|---|---|---|
| CN | 1642593 A | 7/2005 |
| CN | 101420913 | 3/2012 |
| CN | 102512747 | 6/2012 |
| CN | 102781508 A | 11/2012 |
| CN | 102939125 A | 2/2013 |
| CN | 203379465 | 1/2014 |
| CN | 103582508 | 2/2014 |
| CN | 103764218 | 4/2014 |
| CN | 203564643 | 4/2014 |
| CN | 103948972 | 6/2016 |
| CN | 103930158 | 8/2016 |
| CN | 107405158 A | 11/2017 |
| CN | 107405475 A | 11/2017 |
| CN | 108348734 A | 7/2018 |
| CN | 110114108 A | 8/2019 |
| CN | ZL 201080051844.9 | 7/2020 |
| CN | ZL 201580071624.5 | 9/2020 |
| EP | 1604704 | 12/2005 |
| EP | 1809361 | 7/2007 |
| EP | 2254641 | 9/2016 |
| EP | 3215030 | 9/2017 |
| EP | 3215212 | 9/2017 |
| EP | 3349837 | 7/2018 |
| EP | 3541464 | 9/2019 |
| JP | H09-108358 | 4/1997 |
| JP | H09-192226 | 7/1997 |
| JP | 2006501869 | 1/2006 |
| WO | WO 2002/43796 | 6/2002 |
| WO | WO 2002/078511 | 10/2002 |
| WO | WO 2003/051442 | 6/2003 |
| WO | WO 2003/068307 | 8/2003 |
| WO | WO 2003/101310 | 12/2003 |
| WO | WO 2005/076833 | 8/2005 |
| WO | WO 2006/130194 | 12/2006 |
| WO | WO 2008/020980 | 2/2008 |
| WO | WO 2009/117158 | 9/2009 |
| WO | WO 2011/035132 | 3/2011 |
| WO | WO 2013/012714 | 1/2013 |
| WO | WO 2015/187872 | 12/2015 |
| WO | WO 2016/073490 | 5/2016 |
| WO | WO 2016/073511 | 5/2016 |
| WO | WO 2016/116821 | 7/2016 |
| WO | WO 2018/094077 | 5/2018 |
| WO | WO 2020/023749 | 1/2020 |

OTHER PUBLICATIONS

International Search Report and Written Opinion for International Application No. PCT/US2009/001786, dated Sep. 28, 2009. in 8 pages.
International Search Report and Written Opinion for International Application No. PCT/US2010/049297, dated Jun. 21, 2011. in 9 pages.
Japanese Notice of Rejection in Japanese Patent Application 2011-500815 dated Feb. 1, 2013 in 16 pages.
Japanese Notice of Rejection in Japanese Patent Application 2011-500815 dated Jun. 26, 2012 in 7 pages.
Supplemental European Search Report for European Application No. 10817896.3 dated Jun. 19, 2013. in 4 pages.
Supplemental Search Report for European Application No. 09722111.3, dated Jun. 29, 2011. in 2 pages.
U.S. Appl. No. 15/276,575, filed Sep. 26, 2016, Schneider et al.

* cited by examiner

Configuration 1:
Circumferential

Configuration 2:
Partial Circumferential

Configuration 3: patch

Configuration 4: spiral/diagonal

Configuration 5:
longitudal
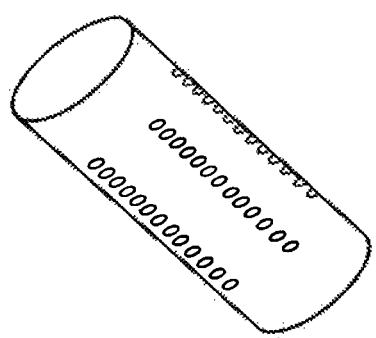
FIG. 9E
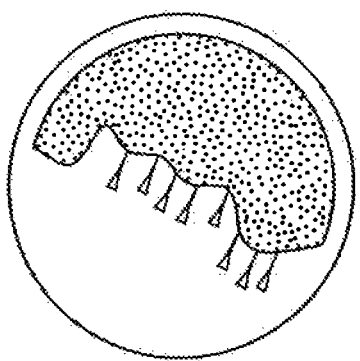 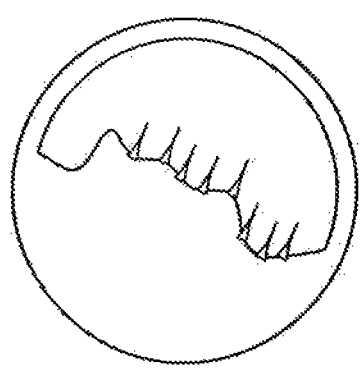 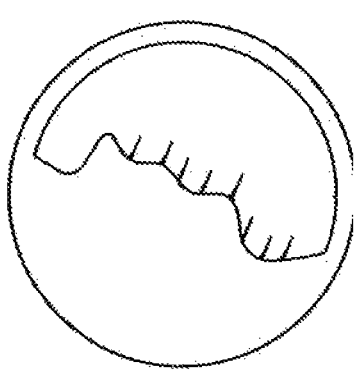
FIG. 13A  FIG. 13B  FIG. 13C

METHOD FOR PLAQUE SERRATION

This U.S. patent application is a divisional application of U.S. patent application Ser. No. 12/562,511 filed on Sep. 18, 2009, which is in turn a continuation-in-part of U.S. patent application Ser. No. 12/408,035, filed Mar. 20, 2009 and now issued as U.S. Pat. No. 8,323,243, which claims priority as a nonprovisional application of U.S. Provisional Appln. 61/038,477, filed on Mar. 21, 2008. All of the foregoing priority applications are hereby incorporated by reference in their entireties.

TECHNICAL FIELD

The present invention is directed to a device and method for opening blood vessels in the body occluded by atherosclerotic plaque by pre-angioplasty serration and dilatation of the plaque.

BACKGROUND

Atherosclerotic occlusive disease is the primary cause of stroke, heart attack, limb loss, and death in the US and the industrialized world. Atherosclerotic plaque forms a hard layer along the wall of an artery and is comprised of calcium, cholesterol, compacted thrombus and cellular debris. As the atherosclerotic disease progresses, the blood supply intended to pass through a specific blood vessel is diminished or even prevented by the occlusive process. One of the most widely utilized methods of treating clinically significant atherosclerotic plaque is balloon angioplasty.

Balloon angioplasty is an accepted and common method of opening blocked or narrowed blood vessels in every vascular bed in the body. Balloon angioplasty is performed with a balloon angioplasty catheter. The balloon angioplasty catheter consists of a cigar shaped, cylindrical balloon attached to a catheter. The balloon angioplasty catheter is placed into the artery from a remote access site that is created either percutaneously or through open exposure of the artery. The catheter is passed along the inside of the blood vessel over a wire that guides the way of the catheter. The portion of the catheter with the balloon attached is placed at the location of the atherosclerotic plaque that requires treatment. The balloon is inflated to a size that is consistent with the original diameter of the artery prior to developing occlusive disease.

When the balloon is inflated, the plaque is stretched, compressed, fractured, and/or broken, depending on, its composition, location, and the amount of pressure exerted by the balloon. The plaque is heterogeneous and may be soft in some areas or hard in others causing unpredictable cleavage planes to form under standard balloon angioplasty. The basic mechanism of balloon angioplasty relies on a combination of actions caused by the balloon exerting pressure on the atherosclerotic plaque, including; compression of the plaque and the fracture of the hard, circumferentially calcified portion of the plaque. Balloon angioplasty causes plaque disruption and sometimes it causes arterial injury at the angioplasty site. Balloon angioplasty is often performed at high inflation pressures, in excess of 4 atmospheres, very commonly at 8 atm and sometimes up to 22 atm. These high pressures contribute to the unpredictable results of balloon angioplasty.

When the angioplasty balloon is expanded with enough pressure to open a hard plaque, dissection often occurs; the hardened areas become disrupted and partially separated from the arterial wall and are prone to lifting up as flaps or chunks. The higher the pressure of balloon angioplasty and the more rapidly the pressure reaches a high level, the more often it produces dissection. The random cleavage planes that are created by the dissection depend upon the composition of the plaque and the pressure exerted upon it. The cleavage planes tend to be wandering, longitudinal lines. The depth of the cleavage planes or fractures that are created by balloon angioplasty varies significantly and may be superficial or may be deep and extend all the way to the media of the arterial wall. To the extent that the cleavage plane goes across the line of flow, that is perpendicular or diagonal to the axial direction of the vessel, there is the potential for partial or complete lifting of a flap. When a flap of fractured plaque has lifted, it may cause acute occlusion or blockage of blood flow, or leave a significant residual stenosis, or may extend to create a larger flap.

Frequently, a segment of the plaque is more resistant to dilatation than the remainder of the plaque. When this occurs, greater pressure pumped into the balloon results in full dilatation of the balloon to its intended size. The balloon is deflated and removed and the artery segment is reexamined, usually using angiography. The process of balloon angioplasty is one of uncontrolled plaque disruption. The lumen of the blood vessel at the site of treatment is usually somewhat larger, but not always and not reliably. Some of the cleavage planes created by fracture of the plaque with balloon angioplasty form dissection. A dissection occurs when a portion of the plaque is lifted away from the artery and is not fully adherent and may be mobile or loose. The plaque that has been disrupted by dissection protrudes into the flowstream. If the plaque lifts completely in the direction of blood flow, it may impede flow or cause acute occlusion of the blood vessel.

The dissection of plaque after balloon angioplasty is treated to prevent occlusion and to resolve residual stenosis. A common practice has been to place a retaining structure, such as a rigid or semi-rigid tubular stent, to hold the artery open after angioplasty and retain the dissected plaque material back against the wall of the blood vessel to keep an adequate lumen open for blood flow. The clinical management of dissection or residual narrowing after balloon angioplasty is currently addressed through the development of increasingly complex stent structures. However, there has been substantial clinical evidence of disadvantages with using stents, including body rejection of a large mass of foreign material, and the emplacement of extensive surface area of a stent that may become sites for re-accumulation of plaque or re-stenosis due to smooth muscle cell growth and intimal hyperplasia.

In juxtaposition to lesions that may develop significant dissection after balloon angioplasty, a substantial proportion of patients do not sustain major dissections as a result of balloon angioplasty. This seems to depend on several factors, including; the location and morphology of the lesion, and the pressure required to dilate the lesion during balloon angioplasty, but is also to some extent unpredictable. This situation does not require a stent. When post-angioplasty blood vessels show no sign or minimal sign of dissection and are left to heal on their own, i.e., when no stent is implanted, especially in the iliac and femoro-popliteal arteries, the rate of acute re-occlusion is low. The long-term success of balloon angioplasty alone in many cases may produce the same or better long-term results than if a stent was emplaced. Balloon angioplasty without stenting therefore remains one of the most common endovascular procedures in arteries and veins through out the body and one of the most cost effective.

When it is deemed necessary that a stent is required at a given site of plaque buildup, it is highly desirable to have the ability to fully dilate the stent within the lesion. This is a problem that has been the focus of intensive investigation and is due to the fact that some lesions are so recalcitrant to dilatation, that they cannot be dilated even at very high pressures.

Accordingly, it is deemed highly desirable to dilate plaque material so as to create a smooth post-angioplasty surface without elevated flaps or dissection, and to reduce the need for post-angioplasty stent placement. It is further desirable to provide a method of dilatation that permits better expansion of the lumen, such that if a stent is required, it allows the stent to be fully opened. In cases where local sites of post-angioplasty dissections or non-smooth lumen walls present themselves, it may be desirable to implant a retaining structure other than a stent which offers a minimal surface footprint and exerts low lateral pressures against the post-angioplasty surface.

SUMMARY OF INVENTION

To overcome the problems and disadvantages of prior practices of dilating plaque material in blood vessels through balloon angioplasty and with or without the use of post-angioplasty stent emplacement, the present invention employs an intravascular device for pre-angioplasty treatment carrying rows or patterns of small sharp spikes that are actuated by an expansion balloon or other apparatus to pierce the luminal surface of atherosclerotic plaque with lines or patterns of microperforations which act as serrations for forming cleavage lines, expansion lines, or planes in the plaque as a preparation prior to balloon angioplasty. When using a balloon actuated mechanism to press the spikes into the plaque to create the microperforations, expansion pressures of a full range may be used, from less than 2 atm to more than 10 atm. This pressure range may only be necessary for the purpose of introducing the spike elements into hardened calcified plaque. When a balloon actuated mechanism is used to create the microperforations, the blood vessel is only being prepared and is, not being fully dilated to its intended diameter. The diameter of the artery is, much larger than the fully expanded diameter of the spike device. Therefore the wall of the artery does not experience high pressure when the spike device is balloon actuated avoiding the danger identified in high pressure balloon angioplasty.

After preparation of the plaque with the microperforation and serration procedure, the plaque can be compressed and the artery lumen safely and accurately dilated and stretched, using low pressure balloon angioplasty, to its intended diameter without creating numerous and substantial dissections and elevated flaps. The microperforation and serration enable the plaque to be dilated more evenly and smoothly and avoid forming random cracks that may lead to dissection and residual stenosis. The plaque, after it has been pre-treated with microperforation and serration, may also be dilated with lower pressure than that which is used in standard balloon angioplasty. The lower intra-balloon pressure (e.g., less than or equal to 4 atm and very often less than or equal to 2 atm) causes less disruption of the plaque, fewer dissections, and less injury to the artery wall. This "low pressure" or "minimal injury" angioplasty is less likely to cause the biological reaction that often follows balloon angioplasty with neointimal hyperplasia or smooth muscle cell replication.

In addition, microperforation and serration permits the plaque to expand with less fracturing or disruption of the plaque during balloon angioplasty. By preparing the plaque using microperforations and then performing a balloon angioplasty at low pressure, the number and severity of dissections is reduced. This decreases the need for stent placement to be used to treat dissection or residual stenosis after balloon angioplasty. The subsequent balloon angioplasty may be performed at low balloon pressures of about 4 atmospheres or less due to preparation of the plaque with perforations, so as to avoid injury to the arterial wall. By performing plaque preparation and then low pressure angioplasty, there is less likelihood of a dissection occurring deeply and exposing the media layer of the artery. Exposure of this artery stimulates thrombus formation by collagen exposure and also stimulates smooth muscle cell growth which later causes neointimal hyperplastic occlusion of the artery. This decrease in number and also decrease in severity of dissection is a key differentiating factor in comparison to cutting or scoring devices.

Preferred embodiments of the perforation and serration device for pre-angioplasty treatment include three varying methods for spike deployment, through mechanical (or electromechanical or micro electromechanical), balloon, and balloon-assist deployment. In a mechanical (or electromechanical or micro electromechanical) deployment method, lines or patterns of spikes protrude from a carrier surface or are extracted from the core of a catheter used for remote delivery. In a balloon deployment method, the spikes are mounted on an expandable balloon (similar to those used in angioplasty). In a balloon-assist method, the spikes are mounted on a carrier surface, and the carrier surface is pushed against the plaque under the expansion force of a balloon. The balloon in this method is used as means to stabilize the spikes within the artery and assist in pushing the spikes into the artery wall. In this method one may or may not use the device to perform arterial expansion without a separate balloon angioplasty procedure. Related methods are provided for insertion of the spikes in a compressed state into the blood vessel and expanding them to the intended shape for plaque microperforation and serration, and then re-seating the spikes for withdrawal. Several variations for spike mounting and delivery, and variations for spike cross-sectional profiles and for placement in lines and other patterns are further disclosed.

Preferred embodiments include a delivery device in which spikes are formed like polymer gum drops on a carrier ribbon or strip which are attached on the surface of an expansion balloon that is folded to a compact state for delivery. Another embodiment has spikes shaped as sharp pins carried on mesh bases and folded into flaps of an expansion balloon. Another embodiment of the delivery device has spikes that are deployed from and retracted back into a mechanical carrier. Another embodiment of the delivery device has spikes carried or projectable from the surface of a catheter carrier and an external multi-lobed balloon for pressing the spikes in circumferential sections against the plaque. Yet another embodiment has spikes carried on an accordion-like structure. The spikes may also be carried on ribbons strips of a slitted metal tube which are biased by shape memory outwardly toward the arterial wall. The spikes may be carried on a button structure for attachment to a carrier, or may be carried on a stretchable mesh structure over an expansion balloon. The spikes may be arranged in various patterns on the delivery device depending on the cleavage planes desired to be formed in the plaque.

The pre-angioplasty treatment of a plaque site may also be combined instead with drug-eluting balloon (DEB) angioplasty or drug-coated balloon (DCB) angioplasty. Due to the various applications of balloon angioplasty, there are a variety of medications that may be used, such as: plaque-reducing medication, thrombus inhibiting medication, inhibitors of cell growth, other biologically active treatments, and stem cell delivery. The intended effect is to have the medication taken up by or adhered to the plaque and/or wall of the diseased artery at the time of balloon angioplasty. The preparation of the plaque and the creation of microperforations enhances the uptake and biological activity of the medication. The creation of new plaque surface area in the depths of each of the microperforations, and also the location of the plaque that has been exposed, in the top layer of the plaque without exposing the medial layer, is further facilitative of the biological activity of the medication.

Other variations for the spike device include having drug-coated tips, or an internal drug-containing reservoir where each spike behaves like a syringe, or where the spikes are medication-eluting or bearing and are detached and left in place after perforation of the plaque. In the latter variation, if the spikes are made of bio-degrading or bio-absorbable material, over time the left-behind spikes are degraded or absorbed and leave behind only the perforation holes. Due to the greater penetration and surface area contacted, the left behind spikes would provide greater infusion of medication into the diseased area. Detachable spikes may also be biased to restrain the area of plaque around the tips acting like a regional staple that tacks the plaque against the wall.

Another variation for the pre-angioplasty treatment is the use of a balloon-restricting mesh over the expansion balloon for restricting its maximum expansion diameter so that it is less than the blood vessel diameter. The mesh minimizes the potential of the balloon to expand beyond the stenosis site into an hour-glass shape, and also limits the amount of pressure that is delivered to the plaque by limiting the balloon to a defined radial expansion. The mesh structure can be include spike buttons or by milled (through grinding, laser cutting, metal extrusion, photolithography, or other means) to form sections with height variations that act as microperforations.

As an alternative to stent emplacement, in cases where one or more local sites of plaque dissections or flaps present themselves after balloon angioplasty, a thin, ring-shaped tack device may be placed at only the location of each specific problem site, so that the amount of foreign material emplaced as a retaining structure in the blood vessel can be minimized and exert only low lateral pressures against the post-angioplasty surface. A novel method and device for applying a ring-shaped tack device as a retaining structure for plaque in the blood vessel is described in commonly owned U.S. patent application Ser. No. 11/955,331, filed on Dec. 12, 2007, entitled "Device for Tacking Plaque to Blood Vessel Wall", which is incorporated by reference herein.

Other objects, features, and advantages of the present invention will be explained in the following detailed description of preferred embodiments with reference to the accompanying drawings.

BRIEF DESCRIPTION OF DRAWINGS

FIGS. 1A-1C illustrate a preferred embodiment of a delivery device in which FIG. 1A shows spikes formed like polymer gum drops on a carrier ribbon or strip, FIG. 1B shows attachment of the strips 16 on a balloon, and FIG. 1C shows a compact folded balloon.

FIGS. 2A-2F illustrate another preferred embodiment of the delivery device in which FIG. 2A shows the spike in the shape of a sharp pin, FIG. 2B shows how the pin is folded into a mesh, FIG. 2C shows the mesh annealed to the outer surface of an expansion balloon, FIG. 2D shows the pin folded into the mesh and under a flap of the balloon, FIG. 2e shows the pins deployed when the balloon is expanded, and FIG. 2F shows a detail view of the base of the pin.

FIGS. 9A-9E illustrate various patterns for arrangement of the spikes on the delivery device.

FIGS. 13A-13C shows a further variation of the spike device in which the spikes are medication-eluting or bearing and left in place after perforation of the plaque.

DESCRIPTION OF PREFERRED EMBODIMENTS

Figure 1C:
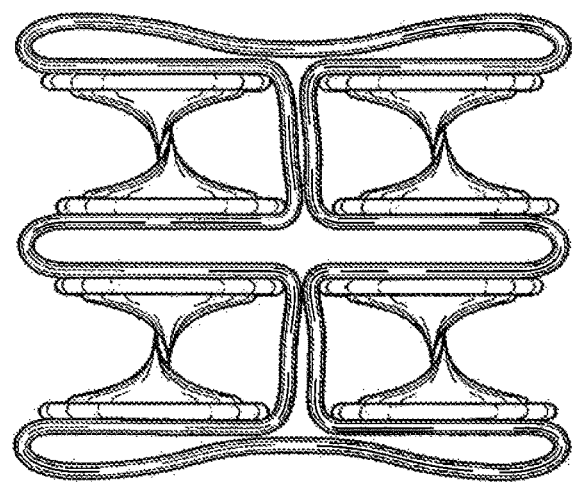

The conventional practice of compression of plaque by expansion pressure during balloon angioplasty, i.e., by applying a high pressure expansion force equally in all directions radially from the inside to a heterogeneous, roughly circumferential plaque structure, can produce unpredictable and inconsistent results. In typical treatment of atherosclerotic plaques, the angioplasty balloon is inflated with 4 to 8 atmospheres of pressure, and pressures up to 22 atmospheres may be required in some cases. Such high pressures can cause injury to the intima and media in the artery at the treatment location. Arterial wall injury is one of the major stimulants to intimal hyperplasia, smooth muscle cell replication and intravascular scarring causing occlusion. Plaque is heterogeneous in nature composed of varying masses of soft and hard materials, calcium and highly variable topography, and can give way along paths of least resistance. Therefore, when standard balloon angioplasty is performed, some of the plaque inevitably fractures. The extent and severity of the fracture, the angiographic result and the morphology of the artery surface that result will vary significantly from one patient to the next. This leads to many cases in which stents are required to be implanted, which prolongs the surgical procedure, and increases medical risk and costs. It also leads to exposure of the medial wall of the artery which causes injury. The reparative process for this injury has been thrombotic and occlusive affects. Moreover, the clinical evidence indicates substantial disadvantages with using stents, including body rejection of a large mass of foreign material, and the emplacement of extensive surface area of a stent that may become sites for re-accumulation of plaque and re-stenosis. There is some evidence that stents may stimulate biological reaction that limits the long-term patency of the procedure. Stents also cause problems with kinking of the artery in areas where the artery is significantly flexed, such as at the knee joint. Stents may also fracture and break due to material stress.

In the present invention, the plaque is treated by a pre-angioplasty preparation procedure of perforation and serration that form lines or patterns of microperforations which act as serrations for forming cleavage lines or planes in the plaque. The serrations will result in more predictable and more uniform expansion characteristics in the plaque during a subsequent balloon angioplasty, thereby helping to make the balloon angioplasty a more consistent and predictable process. It is expected that plaque prepared by the perforation and serration procedure can be dilated with a much lower pressure during angioplasty, i.e., less than about 4 atmospheres, and as low as 2 atmospheres or less. The ability to perform angioplasty at lower pressures will create less plaque dissection and less arterial injury. Less arterial injury may lead to better rates of acute success because there is less dissection, and may also lead to better long-term results since there is less injury to the intima and media in the artery at the treatment location.

The forming of serrations in the plaque through microperforation is deemed to provide a line along which expansion energy may be released. The microperforations are formed in a pre-angioplasty procedure of inserting a carrier carrying an array of small, sharp spikes which are pressed under a slight expansion force to pierce partway into the plaque and without causing injury to the arterial walls. Since plaque usually fractures longitudinally during standard balloon angioplasty, the spikes are preferably arranged in a mostly longitudinal pattern. Other variations include configurations with a diagonal or zig-zag pattern consistent with the expected ways that plaque commonly fractures. The height of the spikes is designed to pierce the plaque surface to create serrations for expansion lines, but not deep enough to cut though the plaque thickness. Materials research on crack propagation can be applied to select the optimal configurations for spike patterning to obtain the best characteristics in plaque compression.

Artery vessels are comprised of organized lamellar structure with repeating structural and functional units of elastin, collagen and smooth muscle cells. The lamellar structure is prone to split and create a cleavage between adjacent elastic lamellae. Basically, in angioplasty the expansion is partly due to the arterial stretching. In addition the plaque material has low ductility and fracture stresses can propagate non-uniform cracks in the brittle material. In the pre-angioplasty preparation of the plaque material, the microperforations act as nucleation sites for void formation. In the subsequent application of balloon angioplasty, stress energy for compressing the plaque is released along the serration created by the series of pinpoint voids formed in the plaque to control crack propagation. If balloon angioplasty is applied without the plaque serration step, the amount of stress energy applied can be very high prior to initiation of crack formation, and once the crack begins the energy can quickly propagate along brittle crack areas, leading to unpredictable plaque ripping, tearing, or dissecting. The plaque does not give way until the force applied by the balloon has overwhelmed the plaque. At that point, the crack or dissection is rapidly propagated along the plaque, thus worsening the dissection. The pre-angioplasty preparation of the plaque with microperforations avoids high stress concentration at an initial point of fracture, and assists stress release along the series of voids designed to guide the fissure event and provide more predictable cleavage lines in the plaque.

The perforation and serration procedure will promote more uniform compression of the plaque under expansion pressure during angioplasty. The portion of the plaque that does not compress will expand better and will be less likely to break or fracture. Forming serrations in the surface of the plaque is expected to provide better and more uniform compression under low pressures in angioplasty and will produce better plaque compression characteristics than the standard approach of applying high expansion pressures against the full length, width, and thickness of the plaque. This is expected to result in compressing the plaque with fewer tendencies for dissection, allowing the plaque to open along more natural lines, and therefore expanding the lumen larger and without causing arterial injury.

The perforation and serration procedure is expected to provide significant advantages as compared to prior proposals for cutting or scoring the plaque with blades or sharp edges during the balloon angioplasty procedure. Some prior proposals have called for performing balloon angioplasty with longitudinal cutting blades affixed to the sides of the angioplasty balloon. However, in order to push the cutting or scoring blades into the plaque, high forces are required. Moreover, at the typical high pressures for balloon angioplasty, the cutting blades or scoring blades forced into the arterial walls experience even higher pressures at the blade interface surface, because all the force of the balloon is concentrated on the projecting cutting blades or scoring wires. This high pressure angioplasty creates unnecessary injury. Because the cutting or scoring action of the blade is performed at the same time as the expansion of the artery with balloon angioplasty, there is no prior preparation of the plaque before balloon angioplasty and there is a risk that the artery itself may be cut and forced open as the pressure is released during the fracturing event. The artery may thus be injured in a traumatic manner and at, high pressures. The deeper layers of the artery, such as the medial layer or deeper may be exposed or cut or scored or otherwise injured by this device, with the pursuant sequella of artery wall injury. Cutting blades, or scoring wires or edges also have relatively long linear lengths that will cut across non-uniform plaque material, producing uneven cuts and uneven pressure distributions. Even smaller cutting blades will encounter at times areas of dense calcification among softer masses that could be fractured by the linear cutting blades or edges. The longitudinally oriented cutting blades or scoring wires may also be placed across normal or less diseased artery wall surface. Cutting or scoring of these areas can not skip areas where there is little or no plaque, creating even more injury. In contrast, microperforations form tiny holes at specific prick points across the plaque mass and taken together as a line or pattern of perforations result in more reliable serrations. If the barbs that create the microperforations encounter normal or less diseased artery surface, there is less likelihood of injury due in part to the shallow depth of penetration since the expansion of the Spike device is intended not to perform simultaneous full diameter angioplasty but to prepare the plaque and is therefore expanded to a much, lesser diameter than intended for the final result for the artery. In addition, if a barb did happen to go into the wall of the artery at a location that is not needed for treatment (that is, plaque preparation), the result would be a punctuate microperoration, not a crater, canyon or crevice, as is routinely created by scoring or cutting devices.

Other prior proposals have suggested scoring the plaque with a metal wire or tabs arranged around an angioplasty balloon in a spiral or double spiral manner. The outer wire or tabs may be forced into the wall of the artery when the balloon is expanded during angioplasty at high pressure. The orientation of the wire on the outside of the angioplasty balloon focuses the expanding balloon pressure on the wire. Therefore the pressure exerted by the wire against the wall of the artery far exceeds the pressure in the balloon generating a very high localized pressure at the working tip of the wire. The wire or tabs may cut deeply into the wall and may cause increased injury beyond that caused by the high pressure alone. In addition, because the wire is wrapped around the balloon in a spiral manner, the distance between the wire windings around the outside of the balloon will change at different balloon diameters. This causes some axial displacement of the wires so that it may actually undermine artery plaque by causing it to "dig up" the plaque. This may even create dissection planes that are more circumferentially oriented (as opposed to longitudinal) and may be more likely to function as flow limiting dissections.

In contrast, the perforation and serration procedure can be performed at low balloon or other expansion pressures. The microperforations are formed by small sharp spikes which can pierce into the plaque without digging it up. Forming tiny prick points with the small spikes will leave most of the surface of the plaque intact, will not injure the arterial wall, and will leave most of the plaque structure intact for more predictable and better compression characteristics. The serrations allow the plaque to be compressed at lower pressures during the following angioplasty. The plaque is also less likely to form dissections, both because it can be treated at lower pressures, and because the plaque has expansion lines serrated in it that allow it to expand in a more orderly manner.

Because the perforation and serration procedure forms small prick points in the plaque, it may also afford a very effective means of distributing anti-plaque medication or other biologically active medication or stem cell delivery into the plaque from a drug-eluting balloon during angioplasty or from a drug-eluting stent after angioplasty. The microperforations may serve to retain more medication within the plaque mass, acting as a portal to the inner structure of the plaque for the medication to work. In the pre-angioplasty procedure, the spikes may also be used as a carrier for drug delivery by coating the spikes themselves with drugs.

The perforation and serration procedure is thus designed as a minimally invasive approach for creating predictable cleavage planes in atherosclerotic plaque in preparation for balloon angioplasty. The cleavage planes are enabled by the serrations formed by numerous small perforations into the plaque in a predetermined pattern on the plaque surface. By creating a preformed expansion line or line of cleavage prior to angioplasty, the artery is prepared so that it will respond to balloon dilatation in a more predictable manner with less likelihood of dissection or elevated surface flaps. The need for stent placement to smooth the artery surface and retain plaque dissections or flaps can thus be significantly decreased.

A suitable device for performing the perforation and serration procedure may be designed in a number of ways, as described below for the following preferred embodiments which are illustrative of the principles of the present invention. Three different methods for spike deployment, through mechanical, balloon, and balloon-assist deployment, are described with respect to certain preferred delivery designs. The locations, length, and configuration of the spikes may be designed for varying types of lesions and arterial sites being treated. For example, heavily calcified lesions may require that the spikes be more closely spaced and penetrate a little deeper into the plaque. Some device designs may only be partially covered with spikes so that the hardest part of the plaque is left alone and serrations are created along a softer portion of the plaque surface. Lesions that are more longitudinally oriented may require spike placements that are farther apart and arranged in a gradual twirling configuration.

Figure 1:
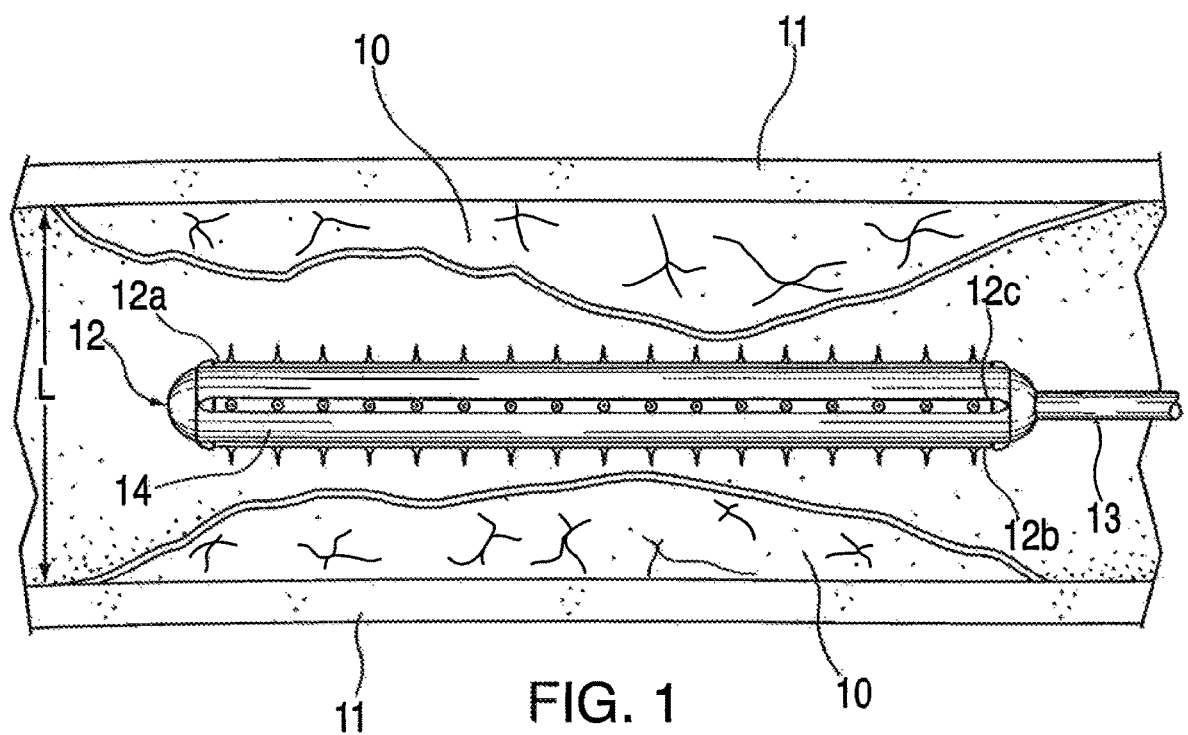
FIG. 1 shows a schematic illustration of the invention method for perforation and serration treatment of atherosclerotic plaque.

FIG. 1 shows a schematic illustration of the invention method for perforation and serration treatment of plaque 10 at a site in an artery 11 with a delivery device 12 for serration and dilatation of the plaque. The lumen L is the flow opening in the artery that has been occluded by plaque 10. The device 12 has one or more arrays 12a, 12b, and 12c of small, sharp spikes carried on carrier strips or surfaces which are seated on the outer surface of an expansion balloon 14 or other expansion device. The spikes are mounted on the carrier strips at spaced intervals and extend typically a distance 0.05 mm to 1.0 mm beyond the carrier surface for piercing into the plaque and forming microperforations across the surface of the plaque. The delivery device 12 may be carried in a catheter and positioned at the plaque site by insertion into the artery through a surgical incision (not shown) and manipulated into position by a wire 13 to the location of the plaque. The spikes and expansion balloon are initially in a deflated or collapsed state to allow threading of the device 12 through the artery.

When the delivery device is in position, and a catheter shield (if used) is retracted, the expansion balloon is inflated through an inlet tube 13 at low gas or fluid pressures to gently push the spike arrays against the plaque 10. Gas or fluid pressures of about 4 atm or less may be used for the pre-angioplasty procedure, and preferably a very low pressure of 2 atmospheres or as low as 1 atmosphere is used. The spikes create series of microperforations which act as serrations along the horizontal length of the plaque. The serrations allow cleavage lines or planes to be formed in the plaque at these locations under compression forces during a following angioplasty procedure. As the spikes are pressed into the plaque, the plaque is also compressed gently for a given measure of dilatation. When the serration has been performed, the balloon is deflated by suction of fluid or gas out through the tube, such that the delivery device 12 can resume its collapsed state so that it can be withdrawn from the artery.

A standard angioplasty balloon may thereafter be used to compress the plaque against the artery walls to open the lumen. The compression of the plaque during angioplasty can take place evenly and with minimal dissection or cracking along the cleavage lines formed by the microperforations. Due to the pre-angioplasty preparation of the plaque, the balloon angioplasty can be performed at low pressures of less than 4 atmospheres, and as low as 2 atmospheres of pressure or less. If the pre-angioplasty procedure has compressed the plaque sufficiently, it may not be necessary to follow it with a standard angioplasty.

Figure 1A:
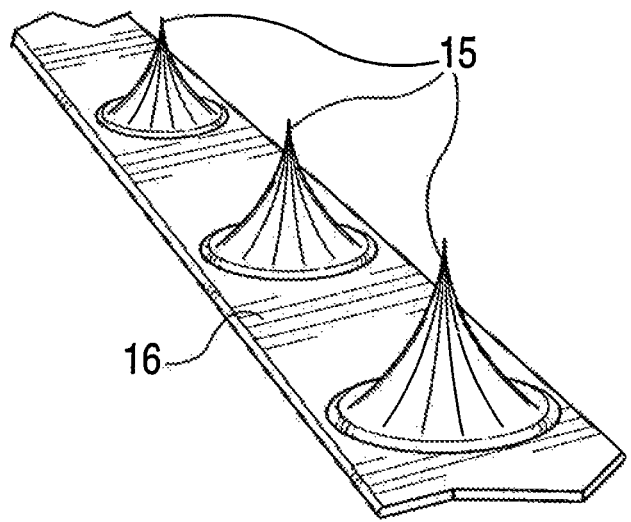

FIG. 1A illustrates a preferred embodiment of the delivery device in which the spikes are formed like polymer gum drops 15 on a narrow ribbon 16. The polymer is heated and fed in liquid form to an ejector that ejects a drop in position on the ribbon. The drop rapidly cools as it is ejected, and forms an inverted cone shape that comes to a hard sharp point by tapering off the fluid from the ejector. The potential shape of the spike can include other types of pointed shapes, such as a long, pyramidal shape, a triangle shape, an arrow shape (longer and sharp in one axis and narrow and dull in the perpendicular axis), a gum drop shape, a narrow rectangle shape, a pin shape, a needle shape, and others. Other materials could be used to form the spike, including a pliable metal, such as Nitinol, or carbon nanotubes.

Figure 1B:
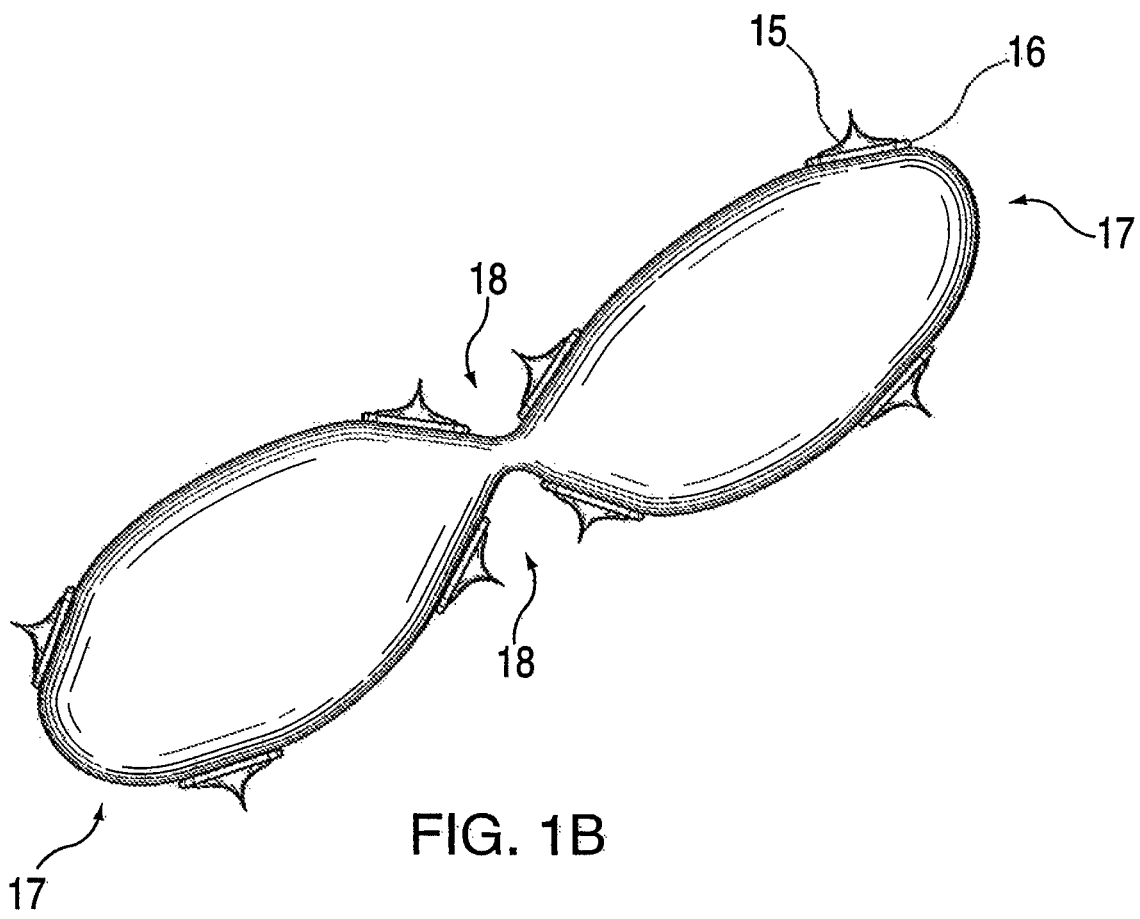

After hardening and processing of the polymer, the narrow strip 16 is annealed to the surface of an expansion balloon or other mechanically expansive carrier. The strips may also be interwoven into a mesh (polymer, metallic, or fabric). The strips or, mesh are arranged in a pattern that envelopes the surface of the expansion balloon or other mechanically expansive structure. FIG. 1B shows attachment of the strips 16 (end view) along the longitudinal length of a balloon 17 at a number (8) of circumferential positions. The balloon may be folded at folds 18 to bring the sharp points 15 on four adjacent strips to nest with those of the other strip, and then the two lobes of the balloon are folded over again to bring the sharp points of the other four adjacent strips into nested configuration. FIG. 1C illustrates the resulting, compact folded balloon in which all the sharp points are folded within to avoid engaging the plaque material when the device is being moved into position.

Figure 2A:
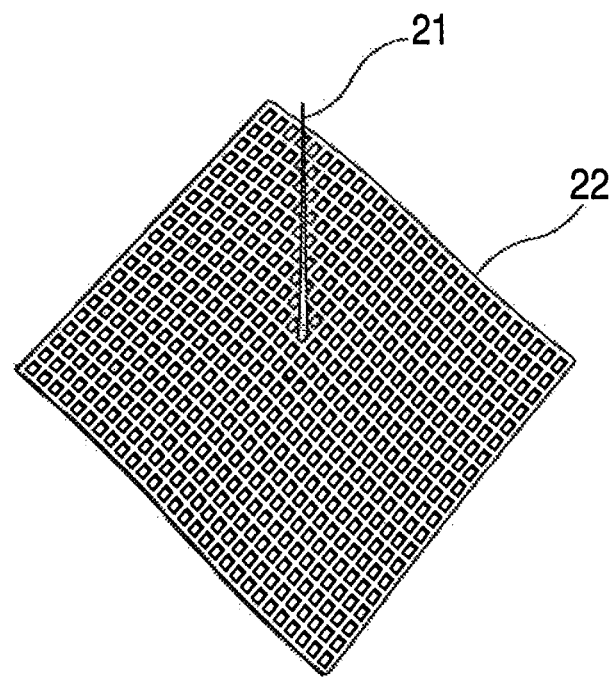

FIG. 2A illustrates another preferred embodiment in which the spike is in the shape of a sharp pin 21 that has a lower end bonded to a mesh 22 that is annealed to the surface of the expansion balloon. The lower end of the pin 21 is held by the polymer mesh so that the spike stands erect on the surface of the balloon when the balloon is inflated. The pin 21 may be constructed of polymer, metal composite, silicon or carbon composite or carbon nanotubes (single or multi wall).

Figure 2B:
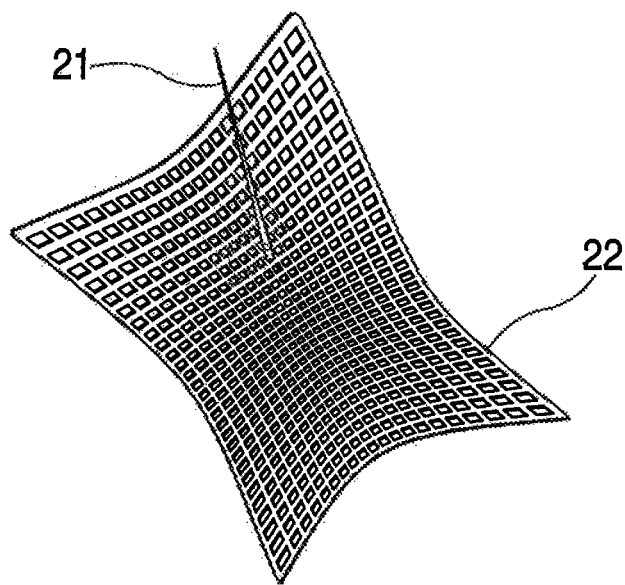
Figure 2C:
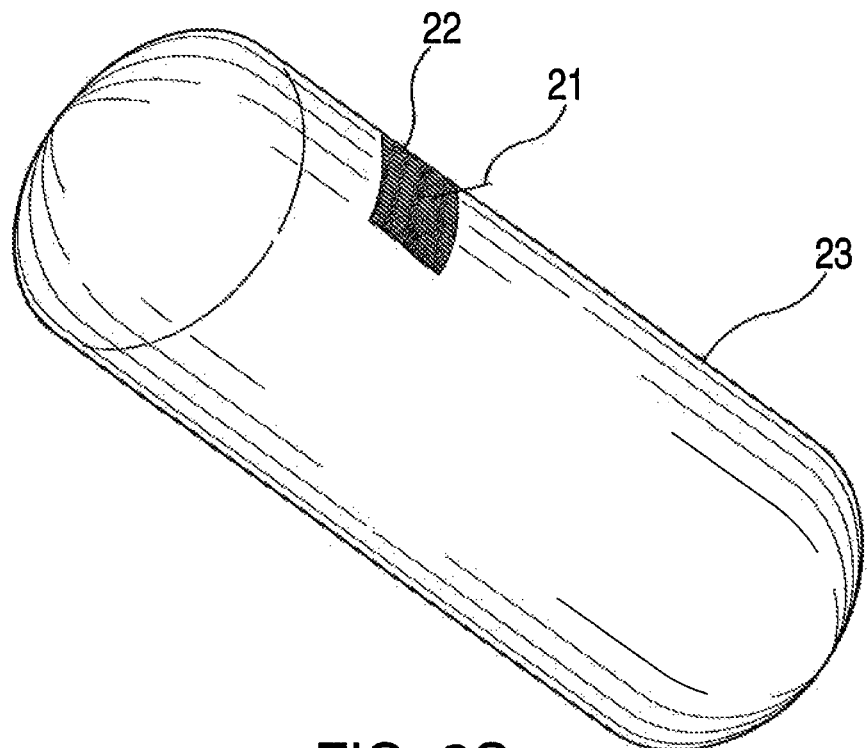
Figure 2D:
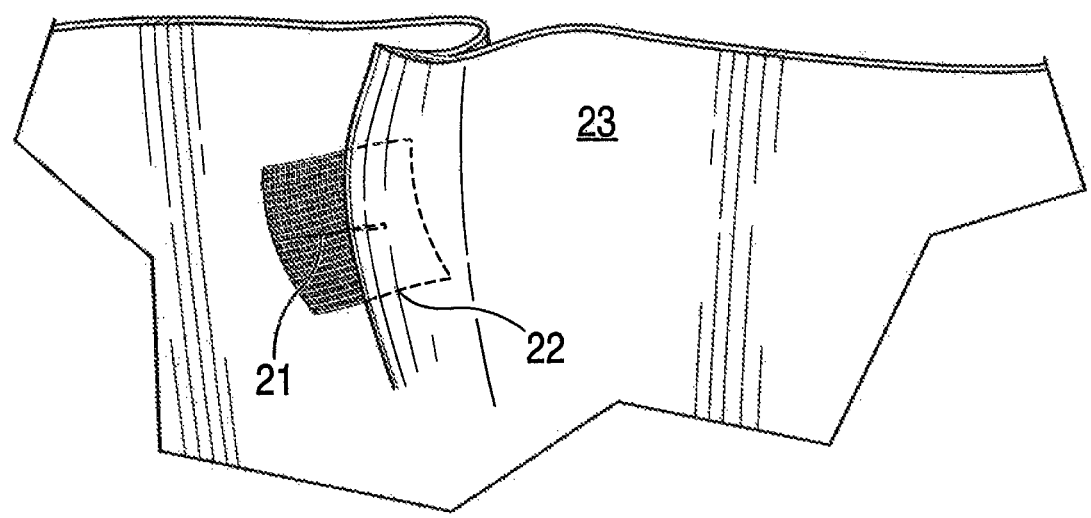

FIG. 2B illustrates how the pin 21 is folded by pressing it into the mesh 22. In FIG. 2C, the mesh 22 is shown annealed to the outer surface of the expansion balloon 23. In FIG. 2D, the pin 21 is laid down laterally and perpendicularly to the axis of the balloon center line for placement, so that the pin is folded into the mesh and under a flap of the balloon. The entire mesh in the depressed mode is nearly swallowed up by the balloon material. With the pin laid down flat within the mesh, the balloon is protected from puncture of the balloon surface. The flap on the balloon unfolds during balloon expansion, and the meshes are unfolded so that the pins are quickly popped out straight and erect.

Figure 2E:
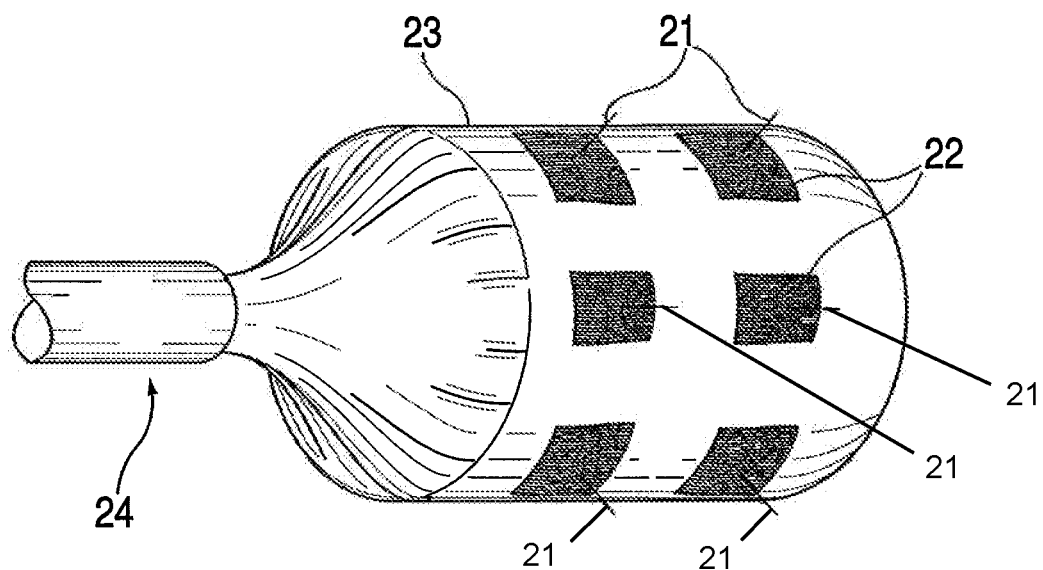
Figure 2F:
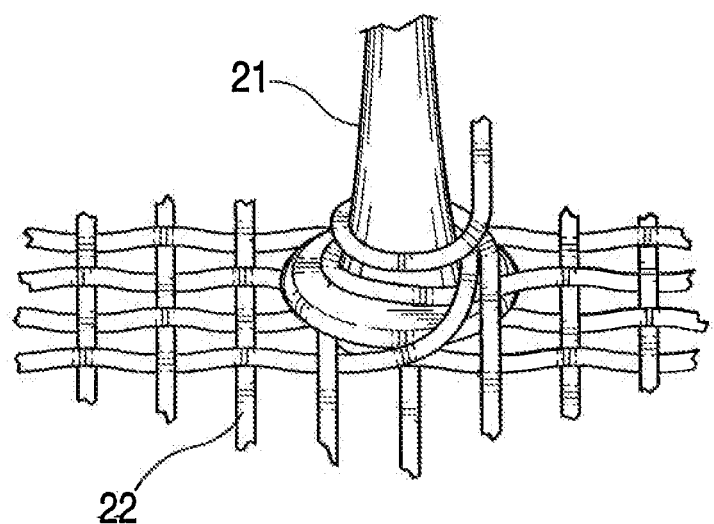

FIG. 2E shows the pins 21 deployed and standing erect on the expansion balloon 23 after the catheter shield 24 is withdrawn and the balloon is inflated. The pins are exposed and stand erect on the mesh sheets 22 that are mounted on the balloon surface. The pins stick out peripherally and can pierce into the plaque as the balloon is further inflated. FIG. 2F shows a detail of the base of the pin 21 entwined in the mesh weaving to center the lower end of the pin on the mesh 22 and hold the pin, erect when the mesh is unfolded and the balloon is expanded.

Figure 3:
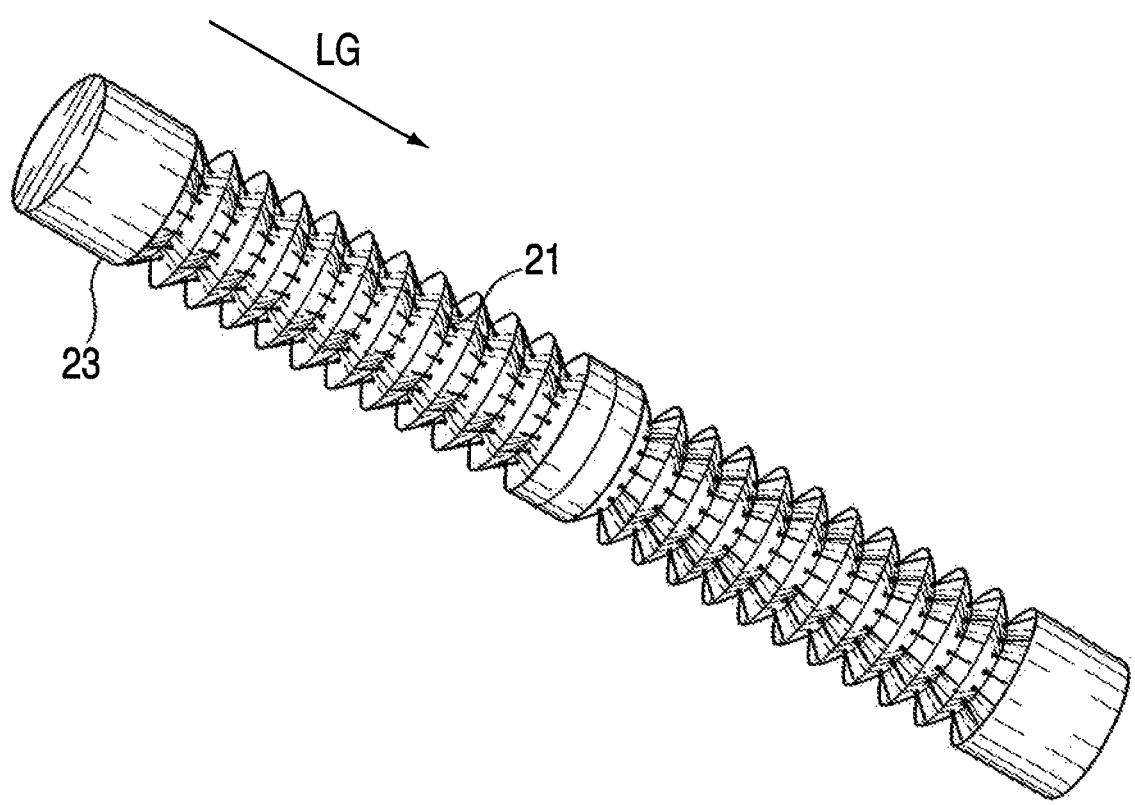
FIG. 3 shows the arrays of pins in the above-described embodiment folded within accordion-like flaps along the length of the expansion balloon.

In FIG. 3, arrays of pins 21 are shown folded within accordion-like flaps of a pre-angioplasty expansion balloon 23 of the device which are folded in alignment with a longitudinal axis LG of the balloon. In this design, half the flaps and pins are folded toward one end of the balloon, and the other half are folded toward the other end of the balloon. When the balloon is expanded, the mesh strips will reorient with respect to the surface of the balloon and face outward toward the plaque on the artery walls. The flaps of balloon material between parallel rows of spikes can be made extra flexible and pliable and may be formed as a folding crease. When gas or fluid pressure is injected in the balloon, the flaps are the first areas to pop out and help to point the spikes outwardly toward the plaque.

Figure 4A:
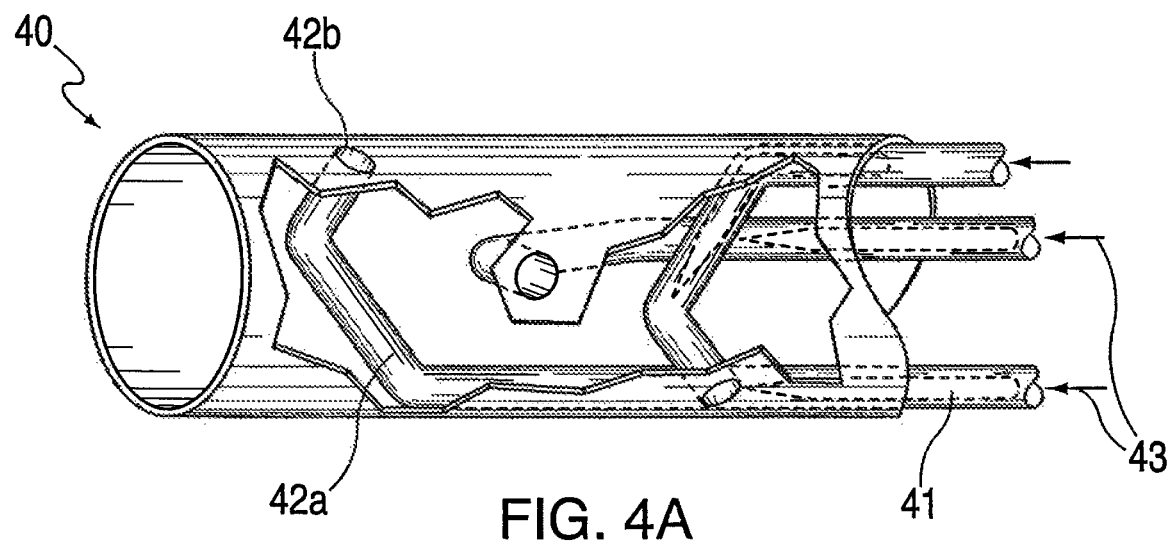
FIGS. 4A and 4B illustrate another embodiment of the delivery device in which spikes are deployed from and retracted back into a mechanical carrier.
Figure 4B:
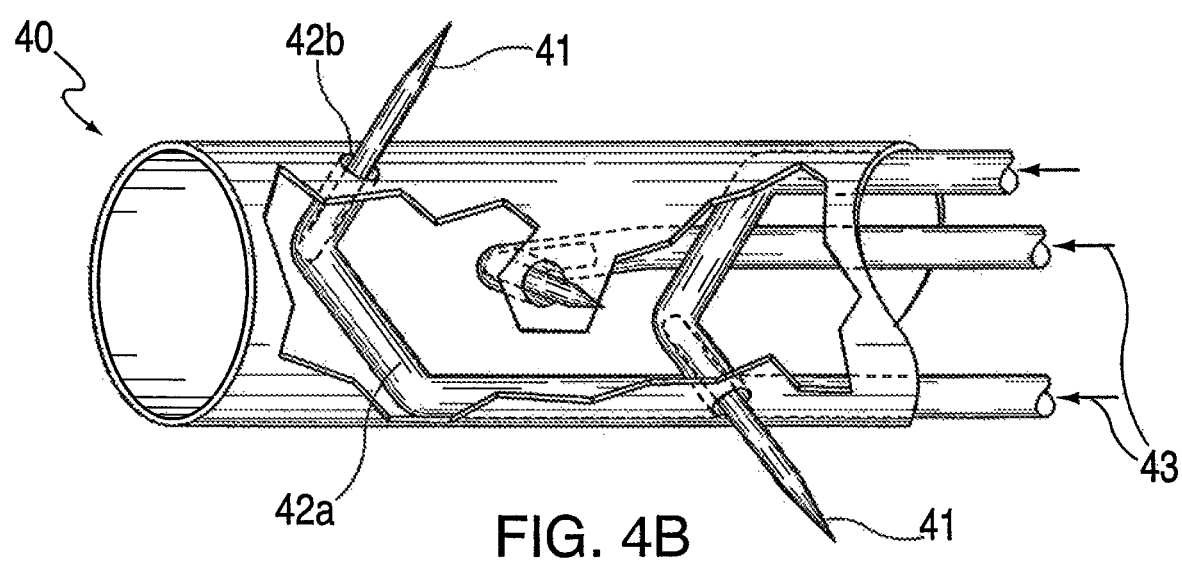

FIGS. 4A and 4B illustrate another embodiment of the delivery device in which an expansion balloon is not used but rather the spikes 41 are deployed from and retracted back into a mechanical carrier 40. The carrier has a plurality of tunnels 42a in its interior each of which holds a spike in a ready position within and has a spike exit hole 42b with its axis oriented radially to the outer surface of the carrier. When the carrier 40 is in position at a plaque site, the spikes are mechanically or hydraulically actuated, such as by an gas or fluid pressure force indicated by arrows 43, to travel through the tunnels and project radially from the spike exit holes 42b. The spikes have sharp points at their tips for creating microperforations in the plaque, but are flexible in their shafts so that they can be deployed from a laying down position and turned to a 90 degree standing up position. In that position, the spikes are pointed toward the wall of the artery and the plaque. As an alternative for mechanical actuation, the spikes may be actuated by respective levers which are pulled or pushed by a cable. Other types of mechanisms similarly may be used for mechanically deploying the spikes from the carrier. This embodiment may also be used to shoot or impregnate the plaque surface with spike devices that are designed to be left in the plaque.

FIGS. 5A-5D illustrate other embodiments of the delivery device for pre-angioplasty serration and dilatation. In the embodiment shown in FIG. 5A, rows of spikes 51 are bonded to a ribbon, rod, triangle or other shaped carrier 50. An outer balloon 52 is divided into quadrants and shaped with cutout areas that conform to spaces in between the spikes. The balloon 52 is inflatable in quadrants circumferentially around the carrier 50. As one quadrant of the balloon 52 is inflated, the spikes on the opposing side of the carrier 50 are pressed into the plaque on the artery wall. The balloon 52 on the side of the one quadrant is deflated, then the next quadrant is inflated to press the spikes on another opposing side into a next section of the plaque. This is repeated for the other quadrants as needed until the spikes on all sides, have been pricked into the circumference of the plaque surface.

Figure 5A:
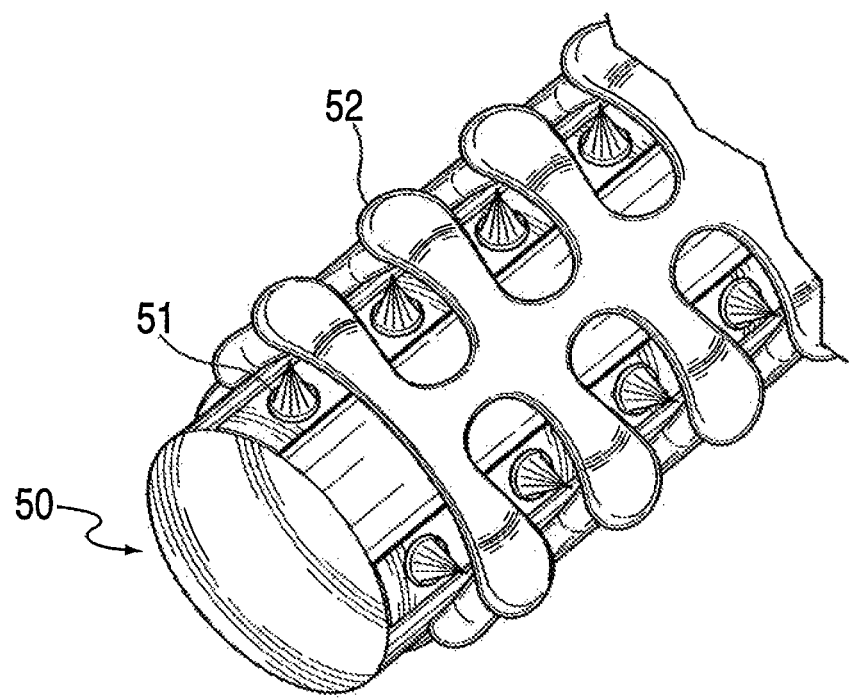
FIGS. 5A-5D illustrate other embodiments of the delivery device which has spikes carried or projectable from the surface of a catheter carrier and an external multi-lobed balloon for pressing the spikes in circumferential sections against the plaque.
Figure 5B:
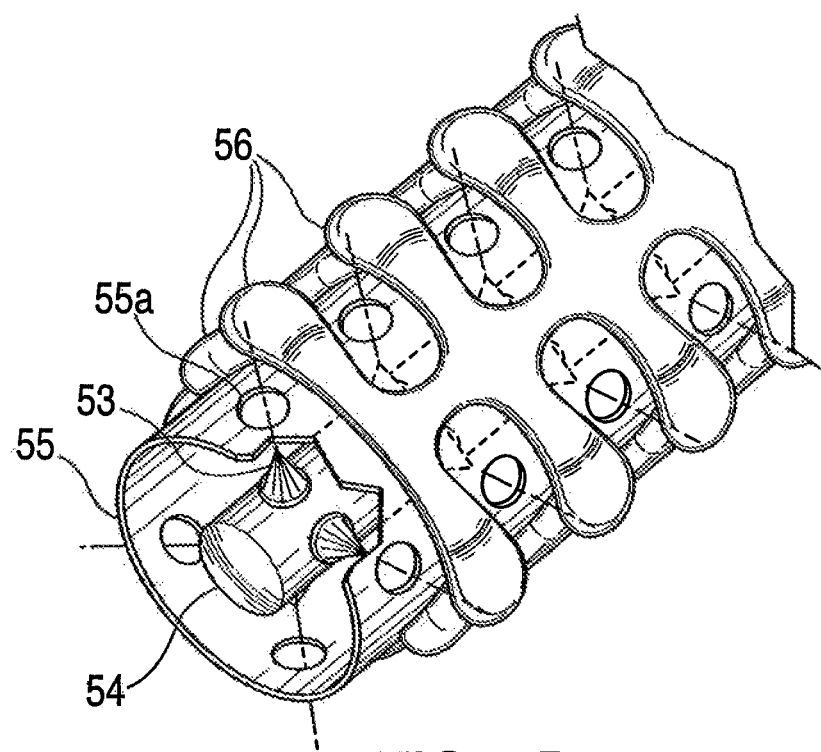

In FIG. 5B, another embodiment of the delivery device has rows or ribbons of spikes 53 bonded to an internal carrier balloon 54 sleeved inside of a tube 55 which has spike holes 55a aligned with the positions of the spikes spacing found on the internal carrier balloon 54. An outer balloon 56 is shaped with cutout areas that conform to the spaces between the spike holes. The outer balloon is able to be filled in quadrants circumferentially around the carrier device. As one quadrant expands, the tube is pressed on its opposing side against the plaque. The internal carrier balloon 54 is inflated and the spikes are pressed out of the holes and pierce into the plaque on the side in contact with the plaque. This is repeated for the remaining quadrants until the spikes have been pricked into the circumference of the plaque surface.

In the above-described embodiments, the multi-lobed segments of the expanding balloon stabilize and support the spikes as they enter the plaque to cause perforation. The spikes may be constructed of any suitable material, such as polymer, pliable metal, or carbon nanotubes, and may have one of many possible shapes, including a pin shape, a needle shape, a long, pyramidal shape, a triangle shape, an arrow shape, a gum drop shape, a narrow rectangle shape, and others. The balloon, as it is expanded, is also used to compress the plaque to a certain degree and dilate the lumen of the artery. The balloon may be manufactured to be inflated with CO2 or with liquid.

Figure 5C:
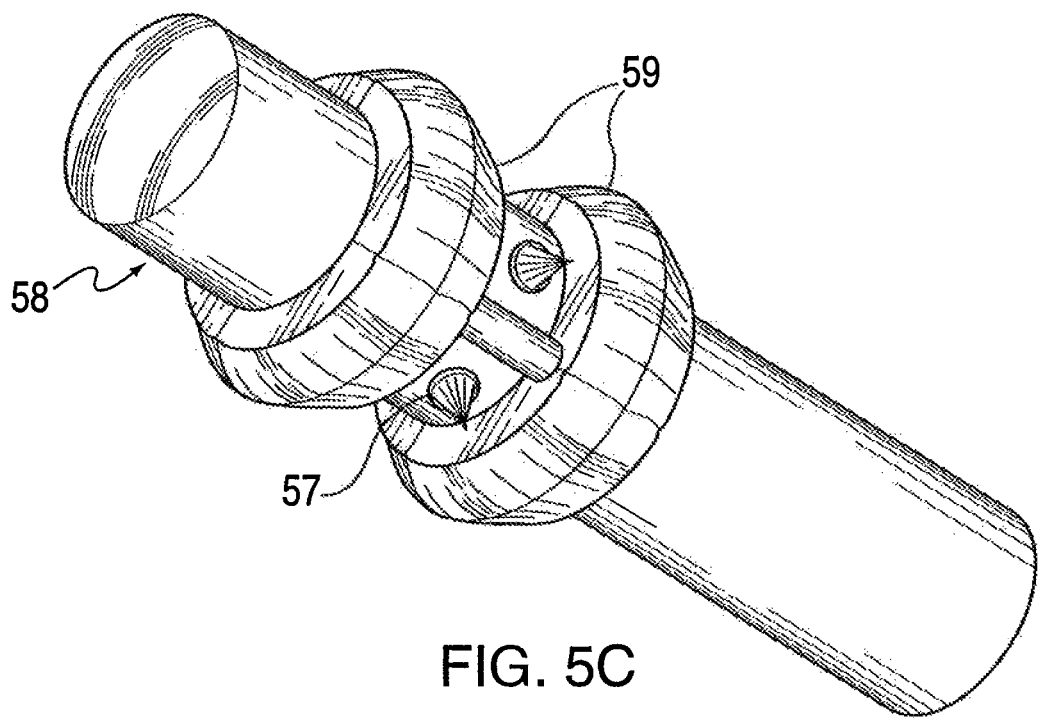
Figure 5D:
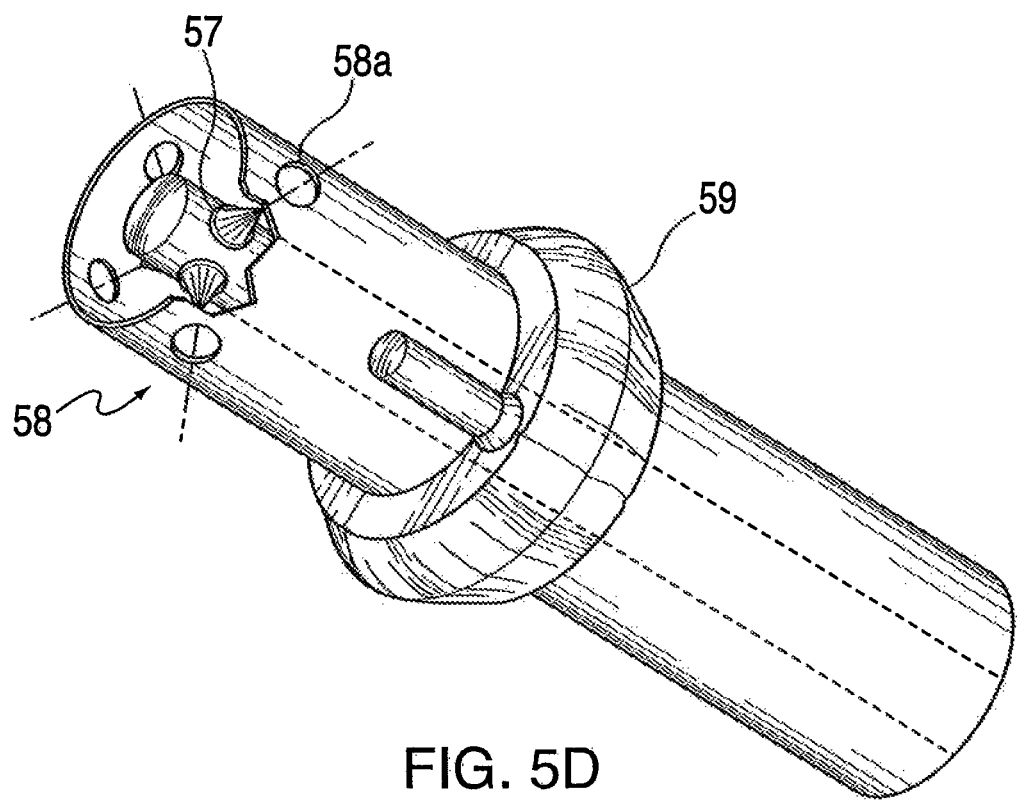

FIG. 5C shows another embodiment where rows of spikes 57 are bonded to or etched out of a ribbon, rod, triangle or other shaped carrier 58. An outer balloon 59 is multi-lobed capable of being inflated in sections and conforming to spaces in between the spikes. FIG. 5D shows a further embodiment in which the spikes 57 are seated on an inner balloon in a delivery catheter 58. The catheter walls have holes 58a located to allow the spikes to poke through when the inner balloon is inflated. On the outside of the catheter in this embodiment is multi-lobed external balloon 59 which is inflatable in sections. As one section is inflated, the catheter wall on the opposite side is pushed against the plaque on the arterial wall, and when the inner balloon is inflated, the spikes 57 are pressed out to pierce into the plaque mass. This procedure is repeated in sections circumferentially around the catheter until all areas of the plaque have been pierced by the spikes.

Figure 6A:
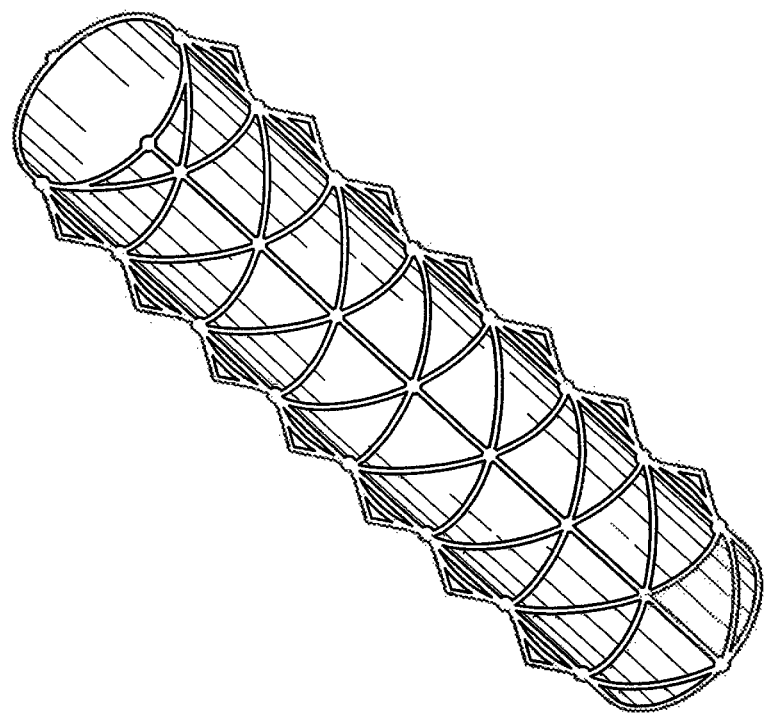
FIGS. 6A-6C show another embodiment for the delivery device in which the spikes are carried on an accordion-like structure
Figure 6B:
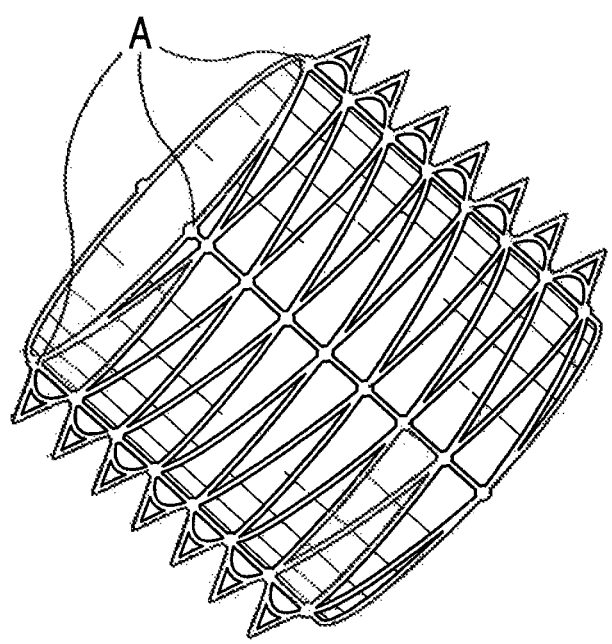
Figure 6C:
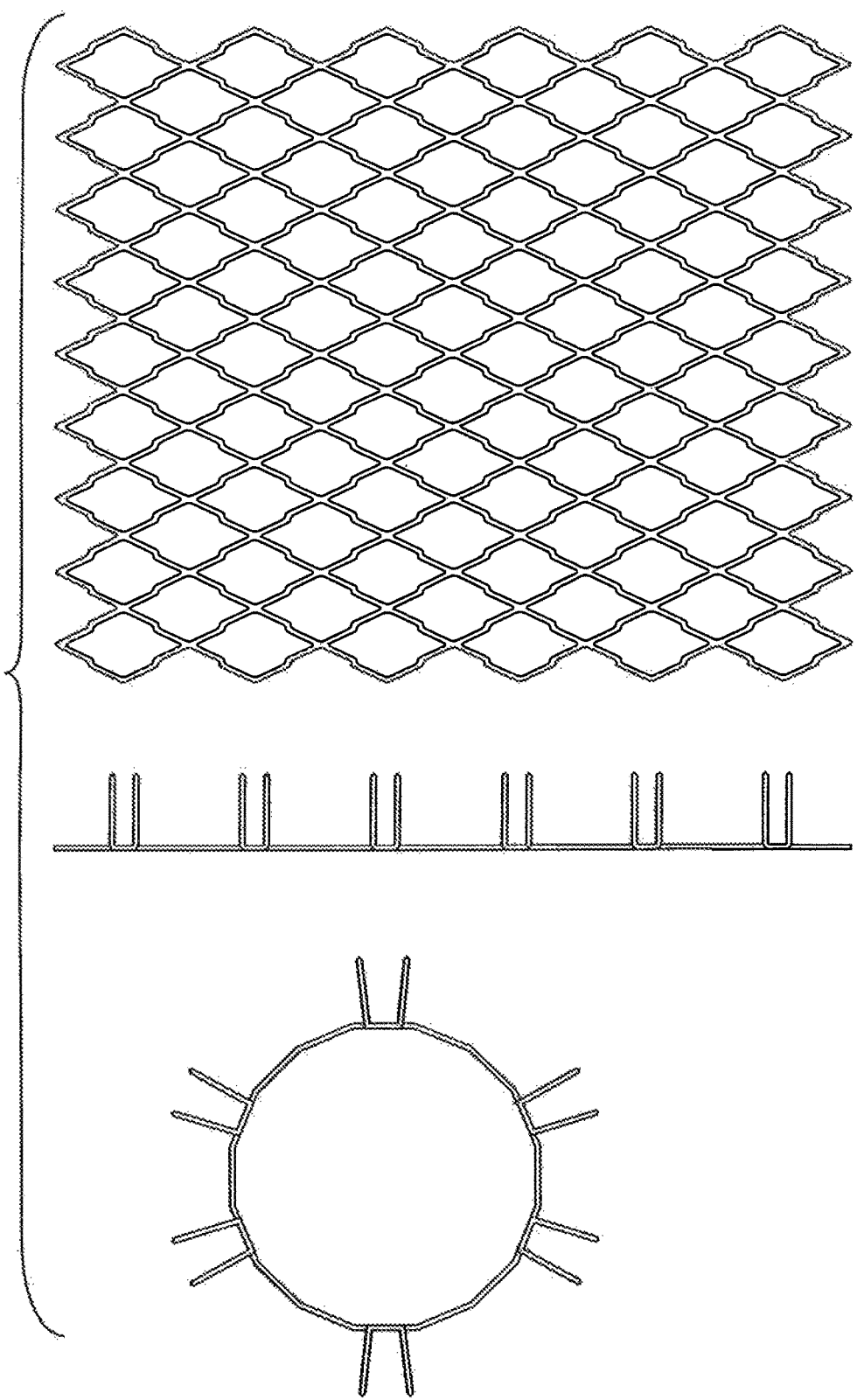

FIGS. 6A-6C show another embodiment for the delivery device in which the spikes (welded, bonded, or shaped out-of-plane) are carried at joints on the circumference of an accordion-like structure provide for a mechanical expansion engagement with the plaque. In the pre-loaded delivery position shown in FIG. 6A, the accordion-like structure 60 is stretched longitudinally over the surface of the delivery catheter 61, and the spikes 62 lay flat against the catheter sheath. This position of the spike structure is used when the catheter is inserted and withdrawn. Once the spike structure is in position at the plaque site, the accordion-like structure 60 has its opposite ends moved together, such that the spikes 62 are pressed out radially to pierce the plaque, as shown in FIG. 6B. The compression of the accordion-like structure 60 may be actuated by mechanical pulley, polymer fiber or wire attached at points A disposed symmetrically around the circumference of the catheter. The wires are pulled uniformly at one end of the accordion-like structure to compress lattice segments of the structure and decrease the distance between the spike connector joints, thereby forcing the spikes outwardly toward the lumen wall. In FIG. 6C, the accordion-like structure is shown laid out in plan view and elevation view, and pre-loaded in end view.

Figure 7A:
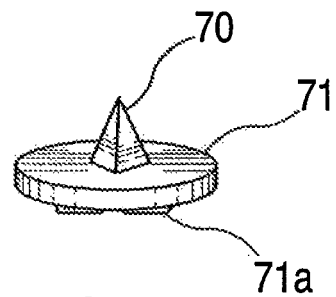
FIGS. 7A-7C show three variations for mounting a spike on a carrier.
Figure 7B:
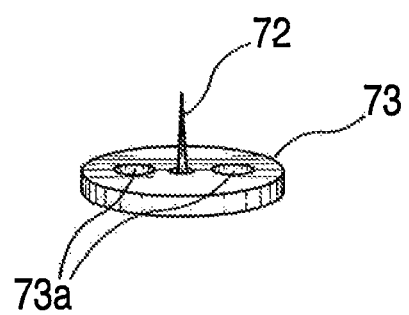
Figure 7C:
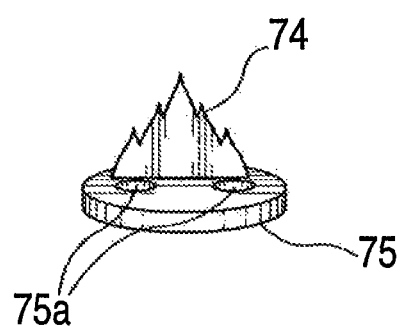

FIG. 7A-7C show three variations for mounting a spike on a carrier. In FIG. 7A, the spike 70 (pyramid point) is mounted on a button 71 having lower shanks 71a for seating on a carrier. In FIG. 7B, the spike 72 (pin) is mounted on a button 73 having button holes 73a for attachment by fasteners to the carrier. In FIG. 7C, the spikes 74 (sharp tips) are mounted on a button 75 having holes 75a for fastening to the carrier. The buttons may be entwined within a fabric, woven pattern or bag structure using the button holes or mounting shanks on the buttons. These spike-mounting buttons may be used with any of the above-described embodiments for the delivery device.

Figure 8:
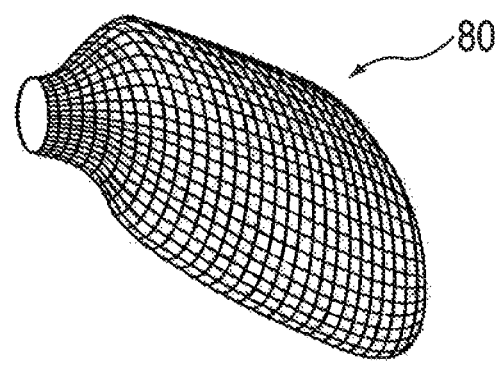
FIG. 8 illustrates an embodiment of the delivery device in which the spikes are carried on a stretchable mesh structure.
Figure 9A:
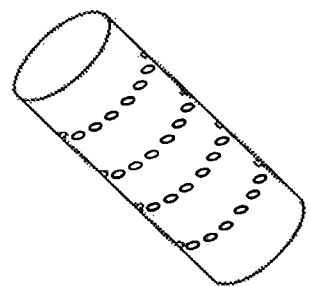
Figure 9B:
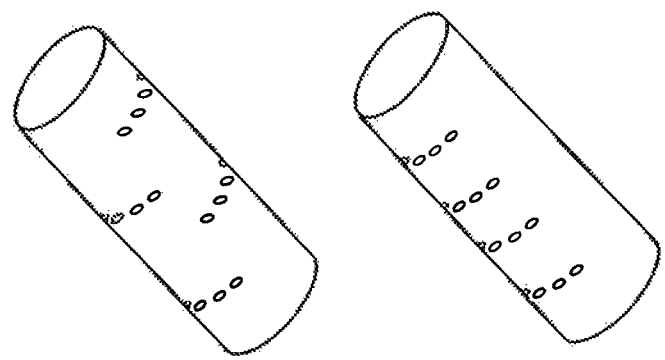
Figure 9C:
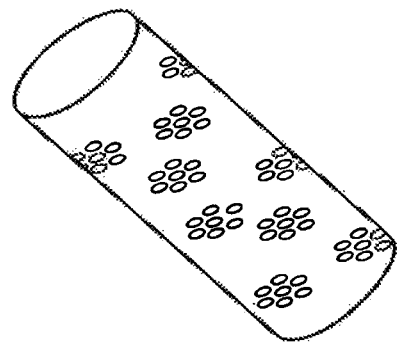
Figure 9D:
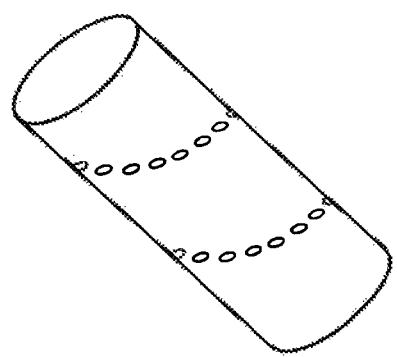

FIG. 8 shows an embodiment in which the spikes are carried on a stretchable mesh structure 80 surrounding an expansion balloon which is inflated to stretch the mesh outwardly on all sides and push the spikes into the surrounding plaque mass. The spikes may be interwoven into the mesh structure. When the balloon is deflated, the mesh snaps back with the collapsed surface of the expansion balloon. Another variation for this embodiment is the use of the balloon-restricting mesh which, when placed over the expansion balloon, the mesh restricts the balloons maximum expansion diameter so that it is less than the blood vessel diameter. The mesh minimizes the potential of the balloon to expand beyond the stenosis site into an hour-glass shape, which is a common problem when the balloon length is longer than the stenosis length. If the balloon spans beyond the plaque on both sides, the inflation pressure in the balloon tends to fill the areas of least resistance first, so it fills on opposite sides of the plaque first. As the balloon pressure increases, the pressure on the healthy vessel walls on the opposite sides becomes equal to or greater than on the diseased portion. The balloon-restricting mesh limits the hour-glass effect and provides a method to control the applied pressure to the region where the lumen needs the expansion. The mesh also limits the amount of pressure that is delivered to the plaque by limiting it to a defined radial expansion. The mesh may be shaped like a "Chinese finger trap" that is restricted in its ability to open, and may be made of nitinol, stainless steel wire, polyethelene filaments, or other inert material.

The balloon restricting mesh prevents bulging of the balloon and evens out the pressure of the balloon on the wall of the artery and prevents too much force from the balloon in any one place and thus limits dissection and damage. In addition, the mesh itself may change the topography of the plaque surface in the same way that microperforations do, i.e., creating many small indentations in the plaque surface so that the plaque can relax evenly when it is dilated.

In all the embodiments described above, the spikes may be made from metal, polymer, silicon or carbon composite (with or without an inert coating), a super-elastic material, or carbon nanotubes. The spikes may have a preferred height (from base to tip) of 0.05 mm to 1.0 mm. The spike tip may be needle-like with a needle head for mounting. As an alternative, the tip can be shaped with a thin tubular cross-section (as in a needle for transporting fluid through it), or a groove or slot having one dimension that is much larger than the other where the larger dimension of the groove is less than 2 mm and the smaller dimension is much less than the first, and a point where the overall head radius is small less than 0.4 mm (as in a pin head), or a collection of very small points where the overall head radius is less than 0.05 mm (as in carbon nanotubes). It may instead be formed by carbon nanotubes presenting a collection of very small points to form a sharp tip. The spikes may also be coated with, or provide transport for, plaque-inhibiting medication for deposition into the plaque site. In the preferred embodiments described above, the spikes may be mounted on the surface of a balloon, or on a catheter, or may be mounted on a mechanically actuated surface. The spikes may have various shapes, may be made from a variety of materials, may be deployed in different ways, and may be attached to the delivery device using different methods. The spikes are arrayed in any desired pattern to create a cut-along-the-dotted-line serration in the plaque mass so that it can become a cleavage plane or expansion plane during dilatation by balloon angioplasty.

The configuration of the spikes may be oriented in different manners depending upon the arterial disease and the plaque formation requiring treatment. The spikes may also have through-holes or inner channels for eluting medication through the spike to the surface of the plaque. The spikes may also be protruding components of the balloon restricting mesh.

FIGS. 9A-9E illustrate various patterns for arrangement of the spikes on the delivery device, i.e., circumferential, partial circumferential, patch, spiral/diagonal, and longitudinal. The configurations are designed for different functional purposes in managing atherosclerotic plaque or in ease of manufacture or ease of use. Plaque with certain characteristics, such as very heavy calcification, may be treated, with spikes that are configured in more of a circumferential or diagonal pattern, crossing the line of blood flow, since this morphology of plaque tends to form clusters or mounds of calcium. The spikes that may not be able to perforate this type of plaque or portions of this type of plaque very readily, but may be able to cut around the areas of worse disease and permit the inner circumference of the whole artery to expand. The spikes are arranged generally longitudinally, consistent with the fracture characteristics of plaque in most situations and with most plaque morphologies, and may be configured in a straight line. The straight, longitudinal lines of spikes may be very short, consisting of five spikes or less and may be quite long, consisting of 100 spikes or more. The longitudinal lines of spikes may be very close together, with as many as 20 lines distributed on the circumference of the artery luminal surface, or there may be as few as a single line of barbs or spikes. The lines of spikes may also be in a slight diagonal or in a zigzag fashion. The configuration of the barbs or spikes is determined in accordance with the best expected mechanism for post-angioplasty plaque dissection. They are designed to create cleavage planes or expansion lines suitable for the expected composition of the plaque and the pressures expected to be exerted upon it. The orientation and depth of desired cleavage planes may vary significantly with the parameters for balloon angioplasty. The spikes may also be constructed so that they may provide delivery of medications. A cooperative structure such as a double-walled balloon for pressure infusion of a small amount of medication agent into the plaque wall or other functionality may also be included.

Figure 10A:
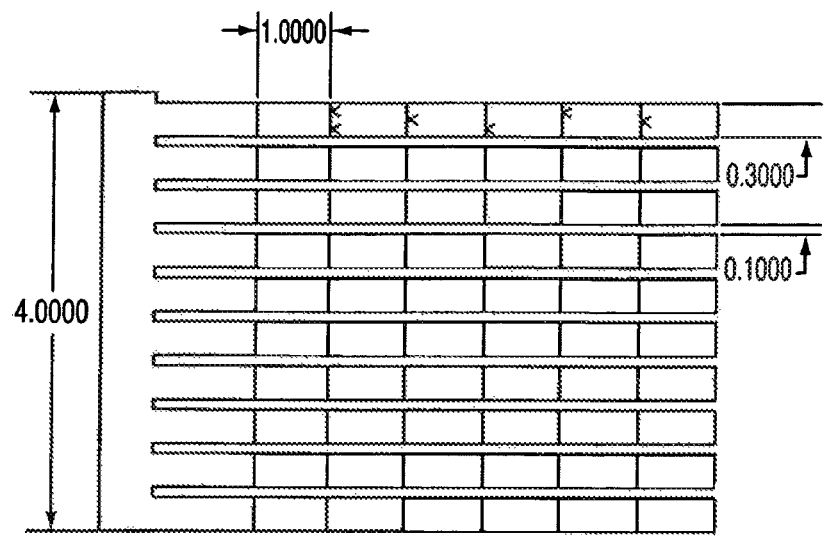
FIGS. 10A-10C show another embodiment for the spike carrier of the delivery device in which the spikes are carried on ribbon strips of a slitted metal tube which are biased by shape memory outwardly toward the arterial wall.
Figure 10B:
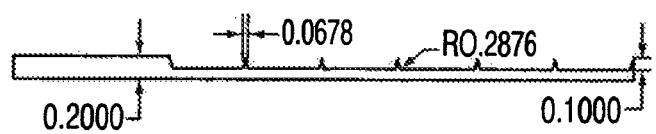
Figure 10C:
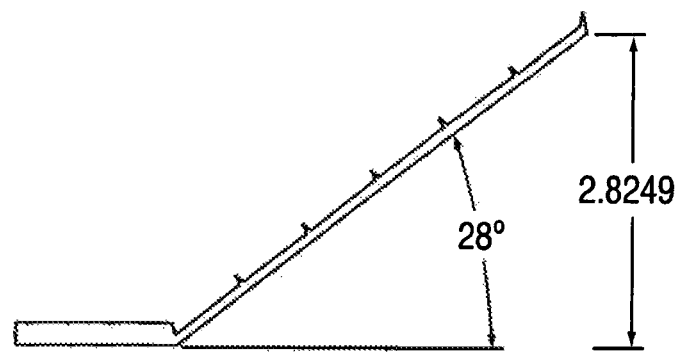

FIGS. 10A-10C show another embodiment for the spike carrier of the delivery device. In FIG. 10A, the spikes are carried on ribbon strips of a sated metal sheet which has opposite ends that are joined by either welding into a tube or the strips are cut out of a tube leaving one end intact. The spikes may have various profiles, such as where the length of the spike base or head is equal to the width of the ribbon strip, or the spike base is a fraction of the ribbon width and is centered at the middle of the ribbon strip, or where the spike base is a fraction of the ribbon width and positioned at varying locations across the ribbon width or may have multiple spikes at any given ribbon section of width. FIG. 10B is an elevation view of the sheet. FIG. 10C shows the sheet after heat treatment to provide a shape memory in which the ribbons are spring-biased radially outward toward the arterial wall for generating perforations in the plaque. The shape memory may be used alone for mechanical engagement of the spikes, or may be combined with an expansion balloon to allow greater control of forces to be applied.

Figure 11A:
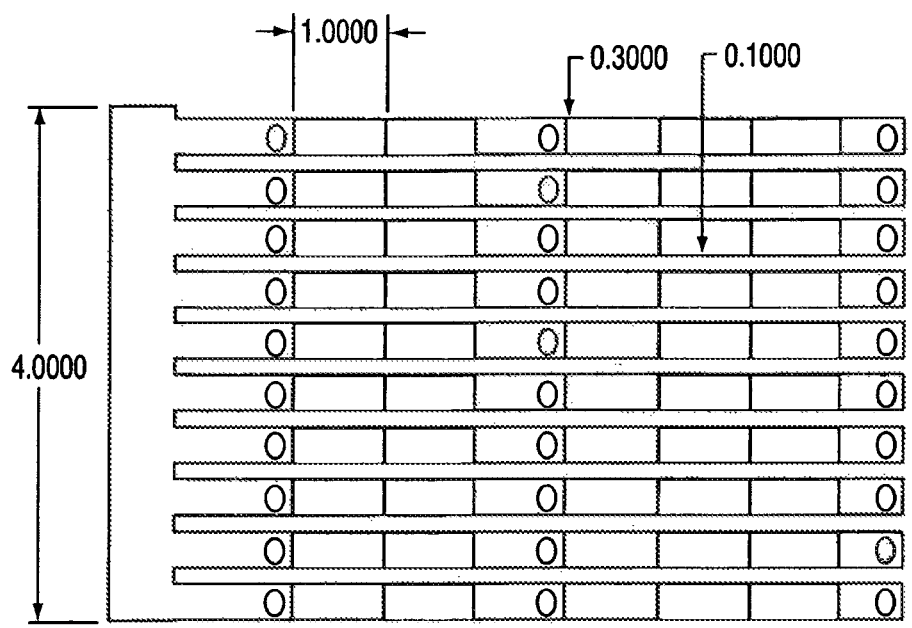
FIGS. 11A-11C show a variation of the above-described embodiment in which the ribbons of the carrier sheet contain a series of holes.
Figure 11B:
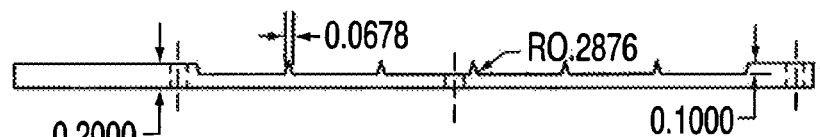
Figure 11C:
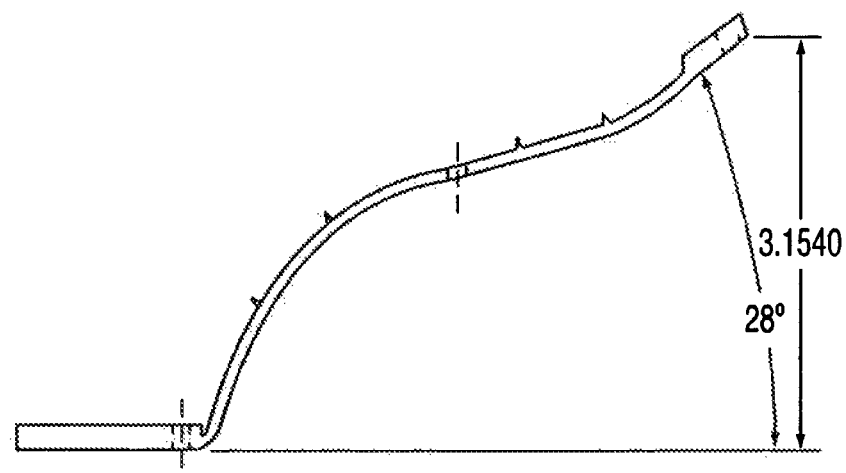

FIGS. 11A-11C show a variation of the above-described embodiment in which the ribbons of the carrier sheet contain a series of holes. The holes serve as points for attachment of strings, cables, or wire elements, configured in such a way, that when pulled can provide additional support and force outward against the lumen wall. FIG. 11B is an elevation view of the sheet. FIG. 11C shows the sheet after heat treatment to provide a shape memory for spring-biasing the ribbons radially outward. The shape memory may be combined with an expansion balloon to allow greater control of forces to be applied.

Figure 12A:
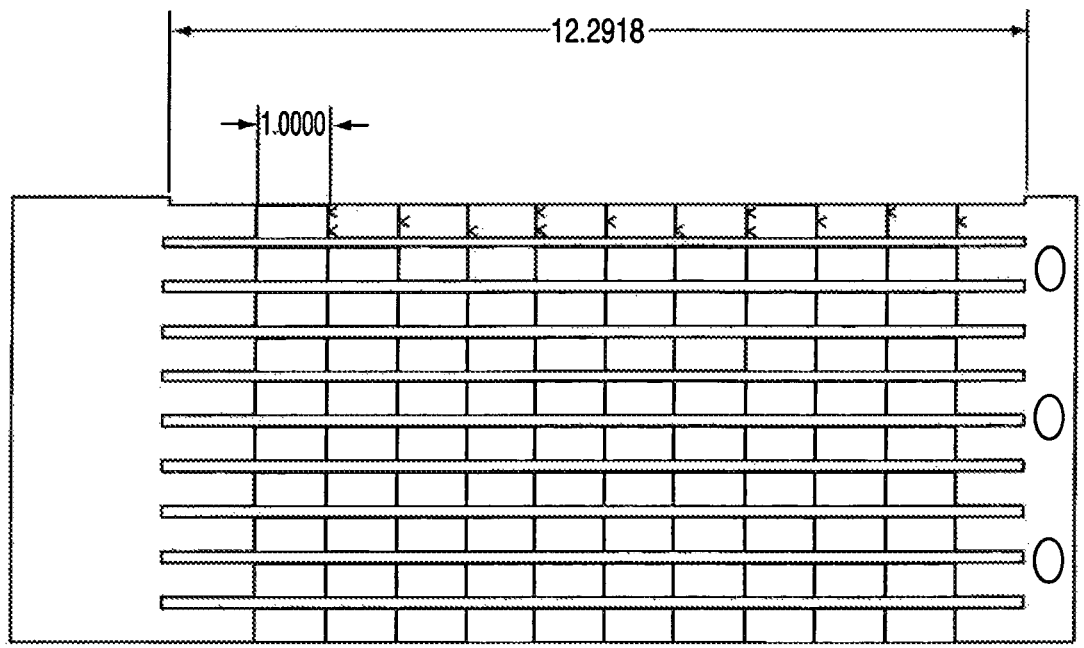
FIGS. 12A-12C show another variation of the above-described embodiment in which the middle section of the carrier sheet has slitted ribbons which are biased outwardly toward the arterial wall.
Figure 12B:
Figure 12C:
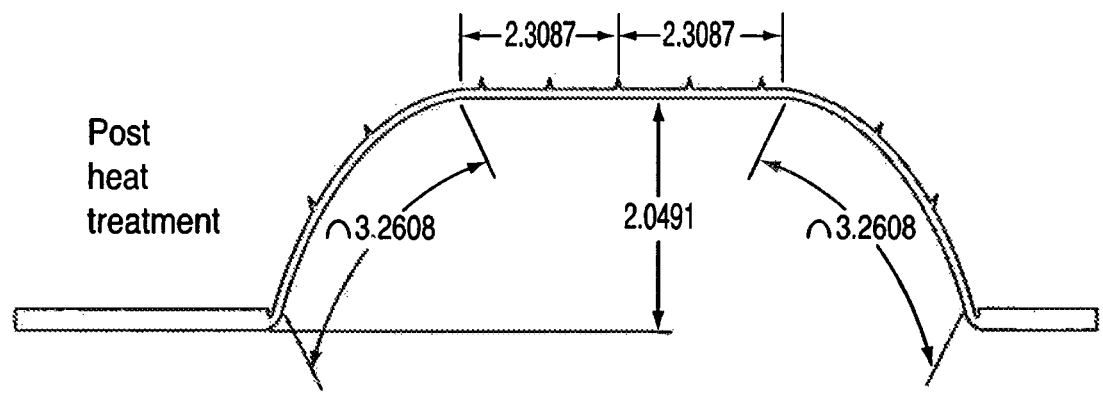

FIGS. 12A-12C show another variation of the above-described embodiment in which both longitudinal ends of the tube are kept intact, leaving only the middle region with slitted ribbons. One end contains a series of holes which serve as points for attachment of strings or wire elements that when pulled can provide additional support and force outward against the lumen wall. FIG. 12B is an elevation view of the sheet. FIG. 12C shows the sheet after heat treatment to provide a shape memory for spring-biasing the middle section of ribbons radially outward.

A general procedure for the pre-angioplasty perforation and serration of a plaque site will now be described. A delivery catheter is constructed for the purpose of plaque perforation in an endovascular environment. A guidewire is threaded along an artery from a percutaneous access site or a surgical incision to a lesion intended, for treatment. A catheter is passed over the guidewire with an end of its sheath maintained gas-tight and fluid-tight for operational control externally by an operator. A spike delivery device is advanced down the hollow, tubular shaft of the sheath over the guidewire and the spike delivery catheter is inserted in position at the lesion. The delivery device for the typical perforation-serration catheter is intended to be as large as 8 Fr and more likely 5 Fr or less in diameter. The guidewire lumen may be 0.014 inch or up to 0.035 inch in diameter. The length of the delivery catheter may be as short as 30 cm but more likely 75 to 80 cm for a short length and 120 to 135 cm for a long length. The catheter has another tubular channel for inflating or actuating the expansion balloon or other actuating apparatus on the delivery end of the catheter.

When the expansion balloon, mechanical expansion apparatus or other apparatus is actuated, the spikes on the delivery device are pressed toward the plaque. The spikes are driven into the plaque and create multiple perforations forming intended serrations in the surface of the plaque in a proscribed pattern. The expansion balloon or apparatus is somewhat compliant and may be inflated further to compress the plaque and enlarge further. However, the device is typically not intended to enlarge the plaque to as large a diameter so as to restore its lumen back to normal and fully intended size. When the desired perforation of the plaque has been achieved, the expansion balloon or apparatus is de-actuated, disengaging the spikes from the plaque, and once collapsed is withdrawn through the catheter sheath.

After the preparation procedure for the plaque, the plaque can be compressed and the artery lumen safely and accurately dilated and stretched during standard balloon angioplasty to its intended diameter without creating numerous and substantial dissections and elevated flaps. The perforation and serration enable the plaque to be dilated more evenly and smoothly and avoid forming random cracks that may lead to dissection, arterial injury, and residual stenosis. The plaque, after it has been pre-treated with perforation and serration, may also be dilated with lower pressure (usually 2 atmospheres or less) than that which is used in standard balloon angioplasty. The lower intra-balloon pressure causes less injury to the artery wall. This "low pressure" or "minimal injury" angioplasty is less likely to cause the biological reaction that often follows balloon angioplasty with neointimal hyperplasia or smooth muscle cell replication. There is less likelihood of exposing or damaging the medial layer of the artery. In addition, the plaque is likely to expand with less fracturing or dissection during balloon angioplasty. This decreases the need for stent placement to be used to treat dissection or residual stenosis after balloon angioplasty. If extensive dissections and non-smooth luminal wall surfaces require a stent to be placed, the improved dilatation of the lumen obtained with pre-angioplasty perforation and serration would allow a stent to be more fully opened.

While there have been prior proposals for providing blades or sharp edges or scoring wire on a balloon during angioplasty for cutting or scoring the plaque in conjunction with balloon expansion, these prior methods are deemed to have problems or disadvantages which are eliminated or avoided by the pre-angioplasty treatment in the present invention. Cutting or scoring the plaque during angioplasty is performed at high pressures that can result in high injury to the blood vessel. The cutting blades, edges or scoring wire are forced into the wall of the blood vessel at the same time that the angioplasty balloon is expanded to dilate the plaque. During this process the cutting blades, edges, or scoring wire can be forced into the vessel wall at oblique angles and can plow up the plaque potentially increasing the tendency for dissections. In contrast, the pre-angioplasty treatment in the present invention employs spike elements that are expanded into the plaque at low pressures so as to form precise microperforations in a radially outward direction that form precise cleavage lines or planes in the plaque. The spikes project sharp points that push into the plaque in small surface areas, thereby being much less likely to plow up the plaque.

For the described embodiments of the spiked device, the depth of the microperforations can be in a range of 0.01 mm to 0.5 mm. The distance between perforations can range from 0.01 mm to 2 mm, and typically may be equal to or greater than the depth of the spikes. The ratio of microperforation spacing to depth preferably is about 1:1 or more. The spikes may also be formed with a serrated edge or a syringe-like point that has one pointed side longer than its opposite side. Another spike head variation can have multiple pointed tips at varying heights. These variations can provide the ability of the spike tip to be perforate into rigid plaque more effectively.

The pre-angioplasty treatment of a plaque site may also be combined instead with drug-eluting balloon (DEB) angioplasty or drug-coated balloon (DCB) angioplasty. In DEB or DCB angioplasty, medication is transferred to the plaque and/or wall of the blood vessel during expansion of the angioplasty balloon at the site of the angioplasty treatment. Due to the various applications of balloon angioplasty, there are a variety of medications that may be used, such as plaque-reducing medication, medications that inhibit tissue in growth, delivery of stem cells and others. The intended effect is to have the medication taken up by or adhered to the plaque and/or wall of the diseased artery at the time of balloon angioplasty. The method of coating the balloon may vary and may include simple placement of the balloon into the medication for a period of time or using an agent that binds the medication temporarily to the balloon. Independent of the coating used, the balloon angioplasty mechanism used in DEB has not been changed significantly from original balloon angioplasty. The balloon is cylindrical in shape and is placed at the site of plaque accumulation and is pressurized. When the pressure accumulates within the balloon, it exerts a force upon the plaque and embeds or coats the plaque with the medication.

If standard DEB angioplasty is used without the plaque-preparation step, the amount of initial surface contact is defined by the morphology of the lumen. The pre-DEB angioplasty preparation of the plaque with microperforations will provide a less rigid and constrained surface. The ability of the atherosclerotic surface to retain a more open structure, accessible to the DEB surface as it expands, is achieved by pre-angioplasty serration. The result is plaque relaxation, opening up numerous microfissure planes, allowing the plaque surface to generate a more uniform intraluminal surface roughness while minimizing the typical tearing associated with angioplasty that generates unpredictable intraluminal surface roughness. The creation of microperforations in the surface of the plaque provides more plaque surface for treatment with the medication that is introduced during the DEB angioplasty. In addition, because the perforations are in the surface of the plaque, the medication will be placed specifically where it will have some effect on the plaque. By adding microperforations, the drug-contacting area is increased, permitting better adherence and uptake of medication.

The following chart summarizes a comparison of impacts and cost factors for traditional angioplasty, DEB angioplasty, and DEB angioplasty with spike preparation:

| Factors for Comparison | Traditional Angioplasty | DEB Angioplasty | Spike prepped Angioplasty |
|---|---|---|---|
| Injury/Plaque Disruption | Severe | Severe | Minimal |
| Pressure on Artery | Severe | Severe | Minimal |
| Stimulates Growth of Re-stenosis | Moderate | Anticipated minimal | Minimal |
| Cost | Higher-more need for stents | Higher-more need for stents | Lower-less need for stents |

As another variation, the spike device can have drug-coated tips, or an internal drug-containing reservoir where each spike behaves like a syringe. A bladder on the outer surface of the spike can be pressed under the expansion pressure of the spike-delivery balloon and injected into the plaque through a capillary in the spike body or along its surface.

FIGS. 13A-13C illustrate a further variation of the spike device in which the spikes are medication-eluting or bearing and left in place after perforation of the plaque. Upon penetration of the spikes into the plaque wall in FIG. 13A, the spikes on the device surface are driven into the wall (through expansion pressure of the balloon) and are left behind as the device retracts, as shown in FIG. 13B. The spike heads that are left behind (like the spines of a porcupine) may offer the following unique functions: (i) capable of injection of medication, STEM cells, or other agents designed to facilitate arterial health; (ii) infused with medication in the spine head surface or through the spine body matrix; (iii) medication contained within a vial in the center of the spines; and/or (iv) fabricated of bio-degrading or bio-absorbable material. If the spikes are made of bio-degrading or bio-absorbable material, over time the spikes are degraded or absorbed and leave behind only the perforation holes, as shown in FIG. 13C. Due to the greater penetration and surface area contacted, the left behind spikes would provide greater infusion of medication into the diseased area. A variation includes spikes where the base is pre-biased to expand laterally capturing surrounding plaque tissue and tacking it to the lumen wall.

As an alternative to stent emplacement following balloon angioplasty, in cases where one or more local sites of post-angioplasty dissections or flaps present themselves, a thin, ring-shaped tack device may be placed at only the location of each specific problem site, so that the amount of foreign material emplaced as a retaining structure for plaque in the blood vessel can be minimized and exert only low lateral pressures against the post-angioplasty surface. A novel method and device for applying a ring-shaped tack device as a retaining structure for plaque in the blood vessel is described in commonly owned U.S. patent application Ser. No. 11/955,331, filed on Dec. 12, 2007, entitled "Device for Tacking Plaque to Blood Vessel Wall", which is incorporated by reference herein. The described procedure for perforation and serration of the plaque performed with a given amount of arterial dilatation may be sufficient to obtain compression of the plaque sufficiently that no balloon angioplasty or stent emplacement is required. Only one or a few of the ring-shaped tacks may be needed to secure the compressed plaque to the artery wall, thereby obtaining the desired medical treatment with minimal forces being applied to the arterial walls and with a minimum of foreign material emplaced in the body. The present invention is therefore deemed to include the alternative of combining the perforation and serration procedure with the procedure for applying localized tacks at specific locations for plaque retention.

Many related benefits, advantageous variations and more functional extensions may be developed or adapted from the above-described principles of the invention, such as the following. In the pre-angioplasty perforation procedure, the spikes may actually be part of a balloon restricting mesh limiting the balloon expansion size, so that if the spikes are placed into segments of the artery with less disease, they do not go into the artery wall because the diameter of expansion of the spikes is kept smaller than the artery size. The pre-angioplasty perforation procedure enables medication from the subsequent DEB angioplasty to be taken up by the artery in greater amounts and with more efficiency. Microperforations may be arranged with, a size, patterning, and strategic positioning relative to the plaque surface that not only optimizes plaque relaxation and expansion but facilitates uptake and activity of medication (including stem cells). The balloon angioplasty performed after perforation preparation is less likely to expose the medial layer of the artery wall, less likely to cause injury. The spikes may be specifically designed for the right size, shape configuration, etc to be optimal for different kinds of plaque. The microperforations can be arranged to create spaces in the optimal places in the plaque for medicine from the DEB to be biologically active. The perforation procedure may also be applied to other tubular structures in the body such as uritor, billiard tree, vena cava, intestines, peripheral veins, Schlemm's canal, and the like.

It is to be understood that many modifications and variations may be devised given the above described principles of the invention. It is intended that all such modifications and variations be considered as within the spirit and scope of this invention, as defined in the following claims.

The invention claimed is:

1. A method for treating an atherosclerotic plaque intravascularly, comprising:
providing an intravascular device comprising a first expandable balloon, a plurality of strips each comprising a base, the plurality of strips operably connected to an outer surface of the expandable balloon, and a plurality of microperforators extending radially outwardly from the base of each of the strips;
positioning the intravascular device at a site in a target vessel proximate the atherosclerotic plaque in a wall of the target vessel;
expanding the expandable balloon to place the plurality of microperforators in contact with the atherosclerotic plaque and create microperforations into the atherosclerotic plaque to form cleavage lines or planes in the atherosclerotic plaque without cutting the atherosclerotic plaque, such that a distance between microperforations is equal to or greater than a height of the microperforators, wherein the distance between the microperforations is from 0.01 mm to 2 mm;
continuing to expand the expandable balloon to allow the microperforations to reach a depth of 0.01 mm to 0.5 mm;
removing the intravascular device from the target vessel;
positioning a separate drug eluting or drug coated device comprising a catheter comprising a second drug eluting or drug coated expandable balloon at the site, the drug-eluting balloon comprising a drug; and
expanding the second expandable balloon to bring the second expandable balloon in contact with the wall of the target vessel and allowing drug to move from a surface of the second expandable balloon into the microperforations.

2. The method of claim 1, wherein a portion of the microperforators is coated with the drug.

3. The method of claim 1, wherein expanding the first expandable balloon is performed at a pressure of less than 4 atmospheres.

4. The method of claim 1, wherein expanding the first expandable balloon is performed at a pressure of less than 2 atmospheres.

5. The method of claim 1, further comprising detaching the microperforators from the intravascular device and into the atherosclerotic plaque.

6. The method of claim 1, further comprising collapsing the first expandable balloon, and withdrawing the intravascular device from the target vessel.

7. A method for treating a blood vessel, comprising:
providing an intravascular device comprising a first expandable balloon, a plurality of strips each comprising a base, the plurality of strips operably connected to an outer surface of the expandable balloon, and a plurality of microperforators extending radially outwardly from the base of each of the strips;
positioning the intravascular device at a site in a target vessel proximate an atherosclerotic plaque in a wall of the target vessel;
expanding the expandable balloon to place the plurality of microperforators in contact with a target region of the blood vessel and create microperforations into the target region of the blood vessel to form cleavage lines or planes in the target region of the blood vessel without cutting the target region of the blood vessel, such that a distance between microperforations is equal to or greater than a height of the microperforators, the distance between the microperforations from 0.01 mm to 2 mm;
continuing to expand the expandable balloon such that the microperforations reach a depth of 0.01 mm to 0.5 mm;
removing the intravascular device from the target vessel;
positioning a separate drug eluting or drug coated device comprising a catheter comprising a second drug-eluting or drug coated expandable balloon comprising a drug at the site; and
expanding the second expandable balloon to bring the second expandable balloon in contact with the target vessel wall and allowing the drug to elute from a surface of the second expandable balloon into the microperforations.

8. The method of claim 7, wherein the second expandable balloon is a drug-eluting expandable balloon.

9. The method of claim 7, wherein the second expandable balloon is a drug-coated expandable balloon.

10. The method of claim 7, wherein the drug comprises a plaque-reducing medication.

11. The method of claim 7, wherein the drug comprises a thrombus inhibiting medication.

12. The method of claim 7, wherein the drug comprises an inhibitor of cell growth.

13. A method for treating a blood vessel, comprising:
providing an intravascular device comprising a first expandable balloon, a plurality of strips each comprising a base, the plurality of strips operably connected to an outer surface of the expandable balloon, and a plurality of microperforators extending radially outwardly from the base of each of the strips;
positioning the intravascular device at a site in a target vessel proximate a wall of the target vessel;
expanding the expandable balloon to place the plurality of microperforators in contact with a target region of the blood vessel and create microperforations into the target region of the blood vessel to form cleavage lines or planes in the target region of the blood vessel without cutting the target region of the blood vessel, such that a distance between microperforations is equal to or greater than a height of the microperforators, the distance between the microperforations from 0.01 mm to 2 mm;
continuing to expand the expandable balloon such that the microperforations reach a depth of 0.01 mm to 0.5 mm;
removing the intravascular device from the target vessel;
positioning a separate therapeutic agent eluting or therapeutic agent coated device comprising a catheter comprising a second therapeutic agent-eluting or therapeutic agent coated expandable balloon comprising a drug at the site; and
expanding the second expandable balloon to bring the second expandable balloon in contact with the target vessel wall and allowing the therapeutic agent to elute from a surface of the second expandable balloon into the microperforations.

14. The method of claim 13, wherein the therapeutic agent comprises a drug.

15. The method of claim 13, wherein the therapeutic agent comprises a stem cell.

\* \* \* \* \*